(12) United States Patent　　　　(10) Patent No.:　US 12,678,568 B2
Kohlbrenner et al.　　　　　　　　　(45) **Date of Patent:　*Jul. 14, 2026**

(54) DEVICE FOR THE DOSED ADMINISTRATION OF A FLUID PRODUCT, ADAPTED FOR THE REPLACEMENT OF A CONTAINER

(71) Applicant: Ypsomed AG, Burgdorf (CH)

(72) Inventors: Philippe Kohlbrenner, Kaltacker (CH); Daniel Kuenzli, Langendorf (CH); Christoph Meier, Utzenstorf (CH); Peter Stettler, Kirchberg (CH); Juergen Wittmann, Burgdorf (CH); Martin Wittwer, Wyssachen (CH)

(73) Assignee: Ypsomed AG, Burgdorf (CH)

( * ) Notice: Subject to any disclaimer, the term of this patent is extended or adjusted under 35 U.S.C. 154(b) by 386 days.

This patent is subject to a terminal disclaimer.

(21) Appl. No.: 18/441,221

(22) Filed: Feb. 14, 2024

(65) Prior Publication Data

US 2024/0252764 A1　　Aug. 1, 2024

Related U.S. Application Data

(63) Continuation of application No. 17/368,936, filed on Jul. 7, 2021, now Pat. No. 11,931,558, which is a
(Continued)

(30) Foreign Application Priority Data

Dec. 31, 2004　　(DE) ..................... 10 2004 063 645.1

(51) Int. Cl.
A61M 5/31　　　(2006.01)
A61M 5/315　　　(2006.01)
(Continued)

(52) U.S. Cl.
CPC .... A61M 5/31583 (2013.01); A61M 5/31533 (2013.01); A61M 5/31553 (2013.01);
(Continued)

(58) Field of Classification Search
CPC .. A61M 5/3202; A61M 5/322; A61M 5/3243; A61M 5/3221; A61M 5/3232;
(Continued)

(56) References Cited

U.S. PATENT DOCUMENTS 4,498,904 A　　2/1985　Turner et al.
4,941,880 A　　7/1990　Burns
(Continued)

FOREIGN PATENT DOCUMENTS

EP　　0338806 A2　　10/1989
EP　　0498737 A1　　8/1992
(Continued)

OTHER PUBLICATIONS

"International Preliminary Report on Patentability", PCT/CH2005/000710, Date of Issuance—Aug. 14, 2007, 26 pages.

*Primary Examiner* — William R Carpenter
(74) *Attorney, Agent, or Firm* — Dorsey & Whitney LLP

(57) ABSTRACT

A device for administering a fluid product includes a first housing part with a receiver for the product, a second housing part detachably connectable to the first housing part, a piston rod held such that it can be displaced for the exertion of an emptying movement, an actuatable or releasable drive element for the piston rod, a coupling element including a coupling input element that couples the drive element to the piston rod in a coupling engagement, transmits a driving force of the drive element to the piston rod, and triggers the emptying movement, and a decoupling element displaceably connected to the second housing part and coupled to the first housing part such that it is displaced, by a movement of the
(Continued)

housing parts in relation to each other when the housing parts are separated into a decoupling position wherein the piston rod is decoupled from the coupling input element.

18 Claims, 12 Drawing Sheets

Related U.S. Application Data continuation of application No. 16/127,951, filed on Sep. 11, 2018, now Pat. No. 11,065,393, which is a continuation of application No. 14/735,991, filed on Jun. 10, 2015, now Pat. No. 10,099,017, which is a continuation of application No. 13/178,893, filed on Jul. 8, 2011, now Pat. No. 9,057,369, which is a continuation of application No. 11/769,496, filed on Jun. 27, 2007, now Pat. No. 7,976,494, which is a continuation of application No. PCT/CH2005/000710, filed on Nov. 30, 2005.

(51) Int. Cl.
| | | |
|---|---|---|
| *A61M 5/32* | (2006.01) | |
| *F04B 49/10* | (2006.01) | |
| *A61M 5/20* | (2006.01) | |
| *A61M 5/24* | (2006.01) | |

(52) U.S. Cl.
CPC .... *A61M 5/31555* (2013.01); *A61M 5/31585* (2013.01); *A61M 5/3204* (2013.01); *A61M 5/3245* (2013.01); *F04B 49/106* (2013.01); *A61M 5/20* (2013.01); *A61M 2005/202* (2013.01); *A61M 5/24* (2013.01); *A61M 2005/3125* (2013.01); *A61M 2005/3126* (2013.01); *A61M 2005/3142* (2013.01); *A61M 5/31535* (2013.01); *A61M 5/31536* (2013.01); *A61M 5/31543* (2013.01); *A61M 5/31558* (2013.01); *A61M 5/31561* (2013.01); *A61M 5/31575* (2013.01); *A61M 5/31593* (2013.01); *A61M 2005/3247* (2013.01); *A61M 5/3257* (2013.01); *A61M 5/326* (2013.01)

(58) Field of Classification Search
CPC .. A61M 5/3245; A61M 5/3257; A61M 5/326; A61M 2005/3254; A61M 2005/3265; A61M 2005/3267
See application file for complete search history.

(56) References Cited

U.S. PATENT DOCUMENTS

| | | | |
|---|---|---|---|
| 5,104,380 | A | 4/1992 | Holman et al. |
| 5,112,317 | A | 5/1992 | Michel |
| 5,114,406 | A | 5/1992 | Gabriel et al. |
| 5,584,815 | A | 12/1996 | Pawelka et al. |
| 5,873,856 | A | 2/1999 | Hjertman et al. |
| 5,938,642 | A | 8/1999 | Burroughs et al. |
| 6,001,089 | A | 12/1999 | Burroughs et al. |
| 6,004,297 | A | 12/1999 | Steenfeldt-Jensen et al. |
| 6,221,053 | B1 * | 4/2001 | Walters ............. A61M 5/31551 604/211 |
| 6,585,685 | B2 | 7/2003 | Staylor et al. |
| 6,663,602 | B2 | 12/2003 | Moeller |
| 6,676,630 | B2 | 1/2004 | Landau et al. |
| 6,796,967 | B2 | 9/2004 | Jensen |
| 7,074,211 | B1 | 7/2006 | Heiniger et al. |
| 7,195,616 | B2 | 3/2007 | Diller et al. |
| 7,513,889 | B2 | 4/2009 | Jost |
| 7,976,494 | B2 | 7/2011 | Kohlbrenner et al. |
| 8,372,042 | B2 | 2/2013 | Wieselblad |
| 9,057,369 | B2 | 6/2015 | Kohlbrenner et al. |
| 10,099,017 | B2 | 10/2018 | Kohlbrenner et al. |
| 11,065,393 | B2 * | 7/2021 | Kohlbrenner ..... A61M 5/31585 |
| 11,931,558 | B2 * | 3/2024 | Kohlbrenner ......... F04B 23/025 |
| 2002/0004648 | A1 | 1/2002 | Larsen et al. |
| 2006/0089594 | A1 | 4/2006 | Landau |
| 2006/0106362 | A1 | 5/2006 | Pass et al. |
| 2006/0258988 | A1 | 11/2006 | Keitel et al. |
| 2007/0167906 | A1 | 7/2007 | Alexandre et al. |
| 2008/0097308 | A1 | 4/2008 | Schiller et al. |
| 2008/0171997 | A1 | 7/2008 | Kohlbrenner et al. |
| 2012/0111186 | A1 | 5/2012 | Kohlbrenner et al. |
| 2014/0107587 | A1 | 4/2014 | Hogdahl |
| 2014/0331996 | A1 | 11/2014 | Elmen |
| 2015/0273157 | A1 | 10/2015 | Kohlbrenner et al. |
| 2019/0001071 | A1 | 1/2019 | Kohlbrenner et al. |
| 2022/0016357 | A1 | 1/2022 | Kohlbrenner et al. |

FOREIGN PATENT DOCUMENTS

| | | | |
|---|---|---|---|
| EP | 0897729 | A2 | 2/1999 |
| WO | 9710865 | A1 | 3/1997 |
| WO | 9938554 | A1 | 8/1999 |
| WO | 02092153 | A2 | 11/2002 |
| WO | 2004002556 | A1 | 1/2004 |
| WO | 2004078240 | A2 | 9/2004 |

* cited by examiner

DEVICE FOR THE DOSED ADMINISTRATION OF A FLUID PRODUCT, ADAPTED FOR THE REPLACEMENT OF A CONTAINER

CROSS-REFERENCE TO RELATED APPLICATIONS

This application is a continuation of U.S. patent application Ser. No. 17/368,936 filed Jul. 7, 2021, issued as U.S. Pat. No. 11,931,558 on Mar. 19, 2024, which is a continuation of U.S. patent application Ser. No. 16/127,951 filed Sep. 11, 2018, issued as U.S. Pat. No. 11,065,393 on Jul. 20, 2021, which is a continuation Ser. No. 14/735,991 filed Jun. 10, 2015, issued as U.S. Pat. No. 10,099,017 on Oct. 16, 2018, which is a continuation of U.S. patent application Ser. No. 13/178,893 filed Jul. 8, 2011, issued as U.S. Pat. No. 9,057,369 on Jun. 16, 2015, which is a continuation of U.S. patent application Ser. No. 11/769,496, filed Jun. 27, 2007, issued as U.S. Pat. No. 7,976,494 on Jul. 12, 2011, which is a continuation of International Application Number PCT/CH2005/000710, filed Nov. 30, 2005, which claims priority to German Application Number DE 10 2004 063 645.1, filed on Dec. 31, 2004, the contents of all of which are incorporated in their entirety herein by reference.

BACKGROUND

The present invention relates to devices for delivering, injecting, dispensing, infusing and administering substances, and to methods of making and using such devices. More particularly, it relates to a devices for injecting or administering a medicinal fluid product. In some embodiments, the device may be an injection apparatus, such as an injection pen, for self-administering the product.

Injection apparatus or devices are well-known from diabetes therapy, administering growth hormones or osteoporosis preparations. Such devices should on one hand guarantee that the correct dosage is administered and, on the other hand, should be simple and convenient to operate.

An injection apparatus known from WO 97/10865 comprises two casing parts which are screwed together. A reservoir containing a product to be administered is accommodated in one of the casing parts, and a conveying and dosing means is accommodated in the other casing part. The conveying and dosing means includes a piston which is accommodated in the reservoir, and a piston rod which acts on the piston in an advancing direction for delivering a settable dosage. The conveying and dosing means also includes a drive member which can be operated by a user for setting the dosage and delivering it. The drive member is coupled to the piston rod via two spindle drives. The piston rod is linearly guided by the casing part which accommodates the reservoir. Once the reservoir is empty, the user has to rotate the piston rod back while simultaneously pressing on the drive member to reuse the apparatus with a filled reservoir.

An injection apparatus comprising a mechanism which is comparable to the coupling between the piston rod and the drive member is known from WO 99/38554.

SUMMARY

It is an object of the present invention to provide a device for administering a fluid product which allows an empty reservoir to be changed simply and reliably.

In one embodiment, the present invention comprises a device for administering a fluid product comprising a first housing part provided with a receiver for the product, a second housing part detachably connectable to the first housing part, a piston rod held such that it can be displaced for the exertion of an emptying movement, an actuatable or releasable drive element for the piston rod, a coupling element comprising a coupling input element that couples the drive element to the piston rod in a coupling engagement, transmits a driving force of the drive element to the piston rod, and triggers the emptying movement, and a decoupling element displaceably connected to the second housing part and coupled to the first housing part such that it is displaced, by a movement of the housing parts in relation to each other when the housing parts are separated into a decoupling position wherein the piston rod is decoupled from the coupling input element.

In one embodiment, the present invention relates to a device for administering a fluid product, comprising at least two casing parts which are detachably connected to each other, one of which forms a reservoir for the product or a space for receiving for a product container, and the second of which forms a bearer for a conveying mechanism. In some embodiments, the conveying mechanism comprises a conveying and dosing mechanism or systems, using which a dosage of the product to be delivered can be set. The conveying mechanism includes a piston rod which is held by the second casing part, a drive member for the piston rod which is also held by the second casing part, and a coupler which couples the drive member to the piston rod in a coupler engagement. The drive member is coupled, in some embodiments, purely mechanically to the piston rod such that operating or triggering the drive member automatically causes a delivery movement of the piston rod, which delivers the product. The product can for example be insulin, a growth hormone, an osteoporosis preparation or another medicine, or in principle even a non-medicine, which can be administered to a human or an animal.

To be able to change the reservoir as simply and quickly as possible, e.g., when it is empty, a decoupling member is provided in accordance with the invention, for which the second casing part also forms the bearer and which is coupled to the first casing part when the casing parts are connected, e.g., via a mechanical engagement which exists directly between the decoupling member and the first casing part. The coupling is formed such that a movement of the casing parts relative to each other, which detaches the casing parts from each other, moves the decoupling member relative to the second casing part into a decoupling position in which it decouples the piston rod from the drive member. The decoupling member holds the coupler in a retracted state, i.e. coupler members which are in coupler engagement for delivery are separated from each other by the decoupling member and the coupler engagement is prevented or, if necessary, released.

Due to the decoupling, the usually extended piston rod can be reset, i.e. retracted, for a reservoir change, without it acting on the drive member. If, in accordance with some preferred embodiments, the drive member is coupled to a dosage display and/or a dosing member, the retracting piston rod does not have a feedback effect on the dosage display and/or the dosing member. Correspondingly, the user does not have to correct the drive member, a dosage display, dosing member or other component of the device after a reservoir change.

In preferred embodiments in which the device is equipped with the option of setting a dosage which may be delivered by a delivery process, its capacity for being set can be configured such that it is set once, for example by a physician, and the user then self-administers the dosage which was set once each time he/she performs a delivery process or operation.

In some preferred embodiments, the dosage can be individually set for each delivery process, such that a user who is self-administering the product can flexibly set the dosages according to requirement. A device which allows the dosage to be set includes a dosing member which can be formed by the drive member or may be provided in addition to the drive member and coupled, mechanically or otherwise, to the drive member such that a dosing movement of the dosing member results in a dosing movement of the drive member.

In a preferred embodiment, a dosage display for displaying the product dosage set is provided. The display can be an acoustic display and/or a tactile display and/or an optical display. The dosage display is coupled to the dosing member, and also to the drive member if the drive member does not already form the dosing member, such that a movement which the dosing member performs when the product dosage is being set causes a change in the product dosage displayed. In the decoupling position, the decoupling member advantageously decouples the dosage display—and/or the dosing member if one is provided in addition to the drive member—from the piston rod in the same way as it decouples the drive member from the conveying member. As applicable, however, the decoupling can also be brought about at a different point on a coupling between the conveying member and the dosing member and/or the conveying member and the display, by holding what is then the other coupler at the relevant interface in a retracted state.

For setting the dosage, the drive member is decoupled from the conveying member even when the casing parts are connected. If the device is additionally equipped with a dosage display and/or a dosing member, the dosage display and/or the dosing member for setting the dosage may also be decoupled from the conveying member when the casing parts are connected to each other. In another preferred embodiment, a dosage display and/or a dosing member for setting the dosage can be decoupled from the conveying member while the drive member is coupled to the conveying member during setting. The decoupling enables the dosage to be freely selected, i.e. the dosage can be increased or reduced, without having a feedback effect on the piston rod.

If the drive member for setting the dosage is decoupled from the conveying member, it is coupled to the conveying member by a coupler movement to cause its delivery movement.

The drive force may be applied manually in one embodiment. In a second embodiment the force may be supplied by a spring drive, which forms the drive member in such an embodiment. In other embodiments, the drive force can also be applied using motors.

If the drive force is applied manually, a path distance of the drive movement is subdivided into a coupler path portion and an adjoining delivery path portion. Once the coupler path portion has been travelled, the drive member is coupled to the conveying member and from then on drives the conveying member over the delivery path portion. In other embodiments, in which the drive force is a spring force or a motor force, the coupler movement is caused by operating a triggering element. As soon as the coupler is relieved of an operating force, motor force or stored force, for example a spring force, to be exerted on the drive member or a triggering element for delivering, the coupling is released automatically. The drive member, or a coupler member which transfers the drive movement, is advantageously charged for this purpose with a restoring force acting counter to the coupler movement to automatically release the coupling between the drive member and the piston rod when the drive member is relaxed. Alternatively, it would also be conceivable for a coupler which is closed for driving the piston rod to be opened, i.e. for the coupler engagement to be released, by the user by manually moving the drive member or alternatively another decoupling member.

In a further development of the present invention, the output-side part of the coupler connected to the piston rod is fixed on the second casing part when the device is in its resting state, such that the piston rod cannot perform a delivery movement, but rather has to be deliberately released, for example directly connected with delivering the product. It is advantageous if the fixation on the casing part is released by the coupler movement. In some preferred embodiments, the coupler engagement is established in a first phase of the coupler path portion of the drive movement of the drive member, or the coupler movement of a coupler member, and the fixation on the casing is released in a subsequent, second phase, advantageously against the elastic restoring force already described. In a preferred embodiment, the coupler includes a coupler intermediate member which on the one hand is in an engagement, which causes the fixation on the casing part, with the second casing part, the decoupling member or another element, and on the other hand is in another engagement with the piston rod, either directly itself or via one or more other intermediate member, wherein the coupler intermediate member is in both engagements when the device is in its resting state, and only in engagement with the piston rod once the coupler engagement has been established.

In some preferred embodiments, the decoupling member is held movably on the second casing part and is in a guiding engagement with the first casing part or an adaptor structure. For the guiding engagement, either the decoupling member or the first casing part forms a guiding curve, and the other forms an engaging element guided by the guiding curve. If an adaptor structure is provided, the same applies to the guiding engagement which is then between the decoupling member and the adaptor structure. When the two casing parts are detached, the decoupling member is moved relative to the second casing part by the guiding engagement, out of a resting position into the decoupling position, and automatically back into the resting position when the casing parts are connected. The guiding curve is therefore shaped such that in the positive-lock guiding engagement, the relative movement of the casing parts when they are released is converted into the movement of the decoupling member relative to the second casing part. Although other mechanisms could also be realized to automatically transfer the decoupling member to the decoupling position when the casing parts are released, for example by a spring force, the embodiment of a guiding engagement enables the path travelled by the decoupling member into the decoupling position, and therefore the decoupling position relative to the second casing part, to be comparatively freely configured. The decoupling member can be moved into the decoupling position, counter to the direction in which the first casing part is detached from the second casing part. Using a guiding engagement, the decoupling member can advantageously be securely locked in the decoupling position, and the locking connection reliably released by connecting the casing parts. In particular, detaching the casing parts can move the decoupling member into the decoupling position, counter to the direction of the coupler movement which establishes the coupler engagement.

Although the coupler can in principle be formed directly between the drive member and the piston rod, by forming corresponding engaging elements on the two members which, in the coupler engagement, are connected to each other in a positive lock, a frictional lock or in a positive and frictional lock, preferred embodiments of the coupler include a coupler output member which is coupled to the piston rod. During product delivery, the coupler output member is driven by the drive member and drives off onto the piston rod. In the decoupling position, the decoupling member decouples the coupler output member from the drive member, while the coupling to the piston rod remains extant. The coupler output member is in direct engagement with the piston rod, said engagement driving the piston rod. The engagement can be a purely positive lock or a purely non-positive lock. It may be formed as a positive and non-positive lock. In some embodiments, it can be a threaded engagement, wherein the thread pitch in the threaded engagement is large enough that a forced translational movement of the piston rod is possible in the direction of the threaded axis when the coupler output member is axially fixed, i.e. the threaded engagement is not self-locking.

The coupler includes a coupler input member which is coupled to the drive member and is in direct engagement with the drive member. The coupling can be a purely positive lock or a purely non-positive lock. In some embodiments, it may be formed as a positive and non-positive lock and/or as a threaded engagement. The threaded engagement is not self-locking such that in the threaded engagement, the drive member can be axially moved by a drive force acting on the drive member in the direction of the threaded axis.

In embodiments in which the coupler input member is driven rotationally in a first threaded engagement, and the coupler output member drives a conveying member translationally via another, second threaded engagement or is in a second threaded engagement directly with the conveying member, the two threaded engagements advantageously form a reducing gear which reduces the path distance of the drive movement to a shorter path distance of the delivery movement. In some preferred embodiments, the reduction measures at least 2:1 or 3:1.

In a preferred embodiment, the coupling between the dosage display and the drive member remains extant in the coupler engagement, such that as delivery progresses, a drive movement of the drive member, counter to the dosing movement, is progressively reset in the same way. If administering is prematurely aborted, whether deliberately or erroneously and unknowingly, the dosage display thus displays the remainder of the dosage set which has not yet been delivered. This can be advantageous when the dosage set is larger than what is still available.

If, as in some preferred embodiments, a dosing member is provided in addition to the drive member, the drive member and the dosing member are advantageously decoupled from each other in the coupler engagement, such that during the drive movement of the drive member no manipulations can be performed on the dosing member which would have a feedback effect on the drive member.

In some preferred embodiments in which the drive member drives the coupler input member rotationally, a spiral spring can form the drive member. The spiral spring is wound around a rotational axis of the rotational movement, wherein at least one outer spring winding surrounds an inner spring winding. The spring exhibits a zero pitch with respect to the rotational axis all over. Using the spiral spring can save on axial length, as compared to springs in which the windings are arranged axially next to each other. One of the two ends of the spiral spring, e.g., its radially inner end, is connected, secured against rotating, to the coupler input member. The other end, e.g., the radially outer end, is connected, secured against rotating, to the second casing part. The coupler input member advantageously forms a reel on which the spiral spring is wound. When setting the dosage, the coupler input member is rotated about the rotational axis, which tenses the spiral spring. A suitable rotational block, for example a ratchet or the like, ensures that the coupler input member can only be rotated in one direction. The rotational block is releasable to be able to correct an incorrectly set dosage. If the rotational block is released, then the worst that can happen if the device is operated erroneously is that the coupler input member is rotated too far back due to the effect of the tensed drive spring. Since the coupler engagement, which couples the coupler input member to the piston rod, has not yet been established when the dosage is being set, since the coupler input member is decoupled from the piston rod, such operational errors cannot affect the piston rod.

In some preferred embodiments in which the coupler includes the coupler input member and the coupler output member, the decoupling member decouples the coupler output member from the coupler input member in the decoupling position. If the coupler engagement is directly between these two coupler members, the decoupling member holds them in a position retracted from each other, in the decoupling position. In some preferred embodiments, the coupler additionally includes a coupler intermediate member which is in engagement with the coupler input member on the input side and with the coupler output member on the output side and so establishes the coupler engagement. It is sufficient for decoupling to release only one of these two engagements of the coupler intermediate member. Alternatively, the decoupling member releases or prevents both engagements of the coupler intermediate member, in the decoupling position. The coupler intermediate member can be the one described in connection with the resting state.

Although the features and developments described herein set forth an injection apparatus comprising a coupler in accordance with the present invention, an injection device in accordance with the present invention need not necessarily comprise the feature of decoupling when changing the container.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the device, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the present invention and/or its components may be selected from appropriate materials such as metal, metallic alloys, ceramics, plastics, etc.

Figures 1, 2, 3:
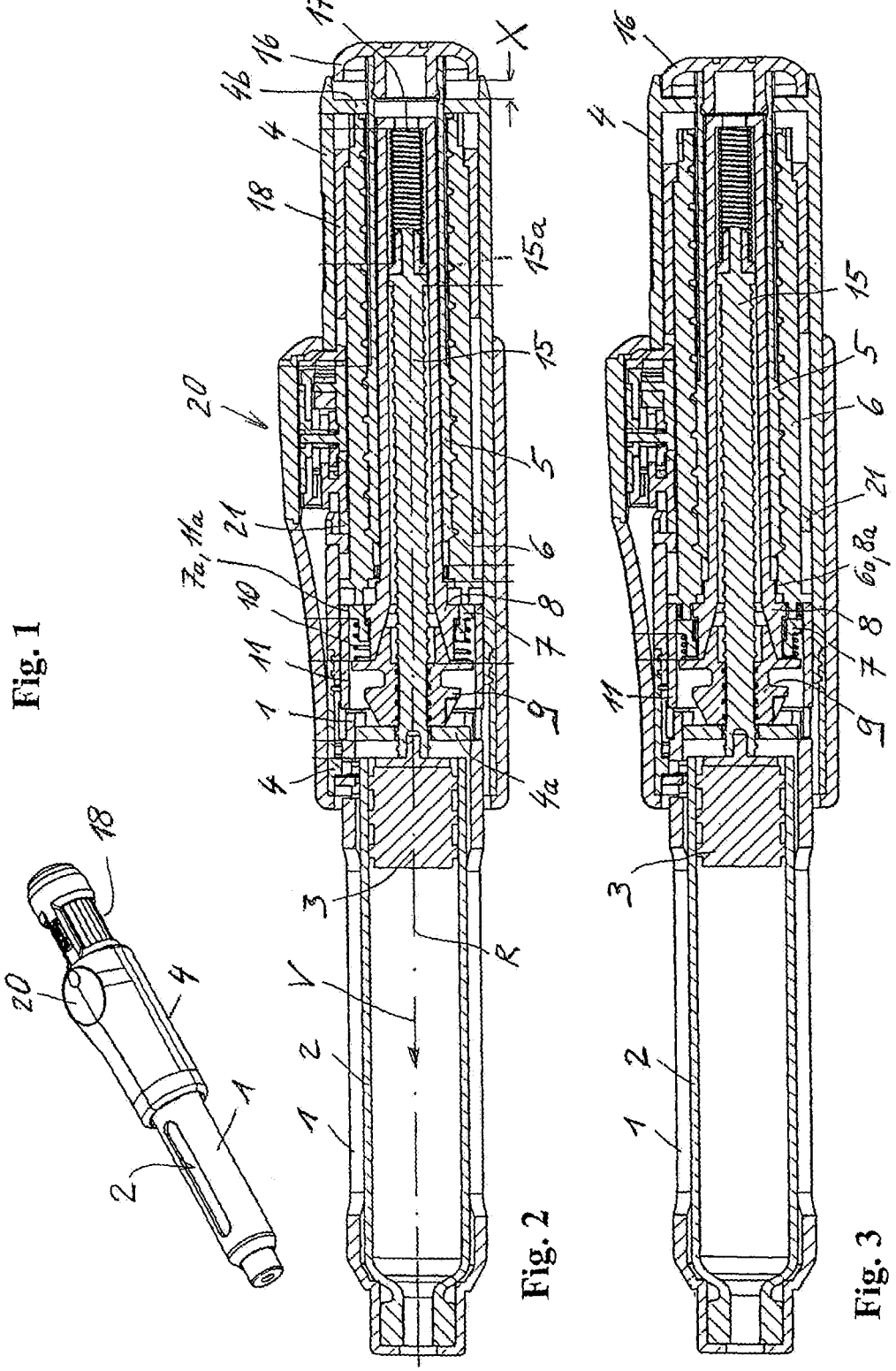
FIG. 1 depicts an injection apparatus of one exemplary embodiment of the present invention, in a perspective view.
FIG. 2 shows, in a longitudinal section, the injection apparatus of FIG. 1, including the coupler thereof, with the coupler open.
FIG. 3 shows the injection apparatus of FIG. 1 with the coupler closed.

FIG. 1 shows one embodiment of the present invention comprising an injection apparatus comprising a first casing part 1 and a second casing part 4 detachably connected to each other. In this exemplary embodiment, the casing parts 1 and 4 are screwed to each other. The injection apparatus is formed as a slim injection pen. The casing part 1 serves to accommodate a container 2 filled with a fluid product and in this sense forms a reservoir, and the casing part 4 serves as a bearer for a dosing and drive means, a dosing member 18 of which can be seen. The casing part 4 is breached in the region of the dosing member 18, such that a user has direct access to the dosing member 18. The dosing member 18 is mounted such that it can be rotated about a central longitudinal axis of the apparatus, and formed as a sleeve which is ribbed on its outer circumference so as to be user-friendly. A dosage display 20 can also be seen, which is laterally placed through a breach in the shell of the casing part 4.

FIG. 2 shows the injection apparatus of the first exemplary embodiment, in a longitudinal section. The container 2 is accommodated in the casing part 1. In the container 2, a piston 3 is accommodated such that it can be moved in an advancing direction V. The piston 3 seals the container 2, fluid-proof, at its proximal end. Advancing the piston 3 in the advancing direction V displaces and delivers product through an outlet of the container 2, e.g., through an injection needle protruding into the outlet and fastened to the distal end of the casing part 1 by a needle holder. The container 2 may be formed in the manner of conventional ampoules. The casing part 1 directly forms a container or ampoule holder. The proximal end of the casing part 1 protrudes into the casing part 4 and is screwed to the casing part 4.

The casing part 4 accommodates a piston rod 15 and other components comprising a dosing and drive means or mechanism. In a dosing and drive line, the dosing and drive means includes a drive member 5 and a coupler which in a coupled state, i.e. in a coupler engagement, couples the drive member 5 to the piston rod 15. The piston rod 15, together with the piston 3, comprises a conveying means. In the coupled state, coupler members 6-10 transfer a drive force exerted on the drive member 5 onto the piston rod 15. No coupler engagement exists in FIG. 2, such that the piston rod 15 is decoupled from the drive member 5. In this decoupled state, the user can set the product dosage to be administered, by a dosing movement of the dosing member 18, e.g., a rotational movement.

The drive member 5 is sleeve-shaped. On its shell outer area, it comprises a thread about a threaded axis R pointing in the advancing direction V. Via this thread, the drive member 5 is in threaded engagement with a coupler input member 6. The coupler input member 6 is also sleeve-shaped and provided with a corresponding inner thread for the threaded engagement. The thread pitch in the threaded engagement is large enough that self-locking cannot occur. The dosing member 18 surrounds the coupler input member 6 and is connected to the coupler input member 6 such that it is secured against rotating and cannot be moved axially. The piston rod 15 protrudes into the drive member 5 and the coupler input member 6.

The piston rod 15 is provided with an outer thread over its axial length. Via the outer thread, it is in threaded engagement with a coupler output member 9 which is provided with a corresponding inner thread. These two threads also exhibit a thread pitch which prevents self-locking in the threaded engagement. The thread pitch is less than the thread pitch in the threaded engagement between the drive member 5 and the coupler input member 6. A coupler sleeve 8 is connected to the coupler output member 9 such that it is secured against rotating and cannot be moved axially. The coupler sleeve 8 and the coupler output member 9 can be regarded as an integral component with respect to the movements between the drive member 5 and the piston rod 15. They may be embodied in two parts and fixedly connected to each other. The coupler output member 9 and the coupler sleeve 8 are mounted in the casing part 4 such that they can be rotated about the threaded axis R of the coupler output member 9 but cannot be moved axially. In the threaded engagement, the piston rod 15 protrudes through the coupler output member 9 and protrudes into the coupler sleeve 8. The equalizing spring 17 is clamped between a proximal end of the coupler sleeve 8 and a proximal end of the piston rod 15 and acts on the piston rod 15 in the advancing direction V as a pressure spring. The equalizing spring 17 presses onto the piston rod 15 via a disc 15*a* which is supported such that it can be rotated on the piston rod 15 and forms a flange of a sleeve placed onto the piston rod 15.

The piston rod 15 is linearly guided in and counter to the advancing direction V in a linear guide 4*a*, such that it cannot be rotated relative to the casing part 1. The drive member 5 is also linearly guided relative to the casing part 4 such that it can be moved in and counter to the advancing direction V, for which purpose the casing part 4 directly forms a linear guide 4*b*.

The threaded axis of the piston rod 15 forms a main movement axis of the device. It forms a rotational axis R for the rotational drive movement of the coupler input member 6 and, via the coupler intermediate member 7, the coupler output member 9. It forms both threaded axes. It also forms the translational axis for the piston rod 15 and the drive member 5.

The coupler also includes a coupler intermediate member 7 and a restoring member 10 which is formed as a pressure spring and charges the coupler intermediate member 7 with an elasticity force acting counter to the advancing direction V. The restoring member 10 is clamped between the coupler output member 9 and the coupler intermediate member 7.

If no force acting in the advancing direction V is exerted on the drive member 5, the restoring member 10 ensures, via the coupler intermediate member 7, that the coupler engagement is released. This state is shown in FIG. 2. The coupler input member 6 is pressed in the advancing direction V until it abuts against the coupler intermediate member 7, and is pressed into a proximal end position by the restoring member 10 via the coupler intermediate member 7. By using the coupler intermediate member, the restoring member 10 holds the coupler input member 6 in a holding position relative to the coupler output member 9 and the coupler sleeve 8 fastened to it. The restoring member 10 and the coupler intermediate member 7 thus form a holding means, acting in a non-positive lock, for the coupler input member 6.

FIG. 3 shows the injection apparatus in a coupled state. A coupler engagement exists between the coupler input member 6 and the coupler sleeve 8. For the coupler engagement, the coupler input member 6 and the coupler sleeve 8 form engaging elements which, in the coupler engagement, establish a rotationally secured connection between the two members 6 and 8 about the threaded axis R pointing in the advancing direction V. The engaging elements co-operate as grooves and springs or teeth which are formed parallel to the advancing direction V and evenly distributed about the threaded axis R.

Figures 4, 5:
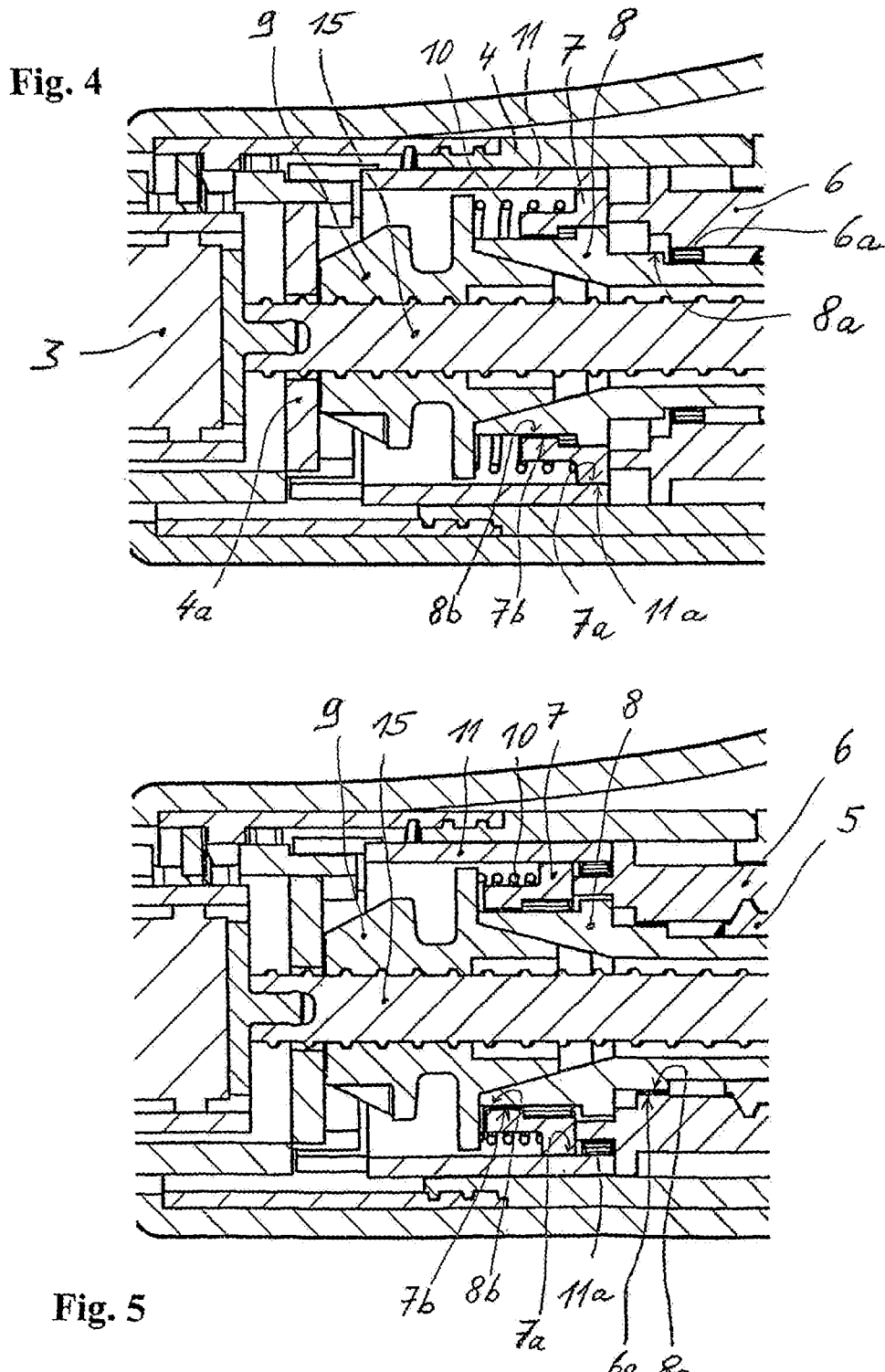
FIG. 4 is a detail from FIG. 2.
FIG. 5 is a detail from FIG. 3.

FIGS. 4 and 5 show the region of the coupler engagement in detail. FIG. 4 shows the apparatus in the decoupled state and FIG. 5 shows the apparatus in the coupled state. FIG. 4 thus corresponds to FIG. 2, and FIG. 5 thus corresponds to FIG. 3.

In the decoupled state, the coupler input member 6 is retracted from the coupler sleeve 8 counter to the advancing direction V, such that the coupler input member 6 can be freely rotated relative to the coupler sleeve 8 and therefore the coupler output member 9 fixedly connected to it. The coupler output member 9 is simultaneously connected, such that it cannot be rotated, to the casing part 4 via the coupler sleeve 8, the coupler intermediate member 7 and a decoupling member 11. For this rotationally secure coupling, the coupler intermediate member 7 is provided with engaging elements 7*b* on an inner area radially facing the coupler sleeve 8, and the coupler sleeve 8 is provided with corresponding engaging elements 8*b*. For the rotationally secured engagement with the decoupling member 11, the coupler intermediate member 7 is provided with engaging elements 7*a* on an outer circumferential area, and the decoupling member 11 is provided with radially facing engaging elements 11*a* on a shell inner area which, in the decoupled state, interlock with each other—like the engaging elements 7*b* and 8*b*—in the manner of grooves and springs or teeth parallel to the advancing direction V. The coupler intermediate member 7, in its rotationally secured engagement with the coupler sleeve 8 and its rotationally secured engagement with the decoupling member 11, can be moved axially in and counter to the advancing direction V, wherein the engagement with the decoupling member 11 is released when it moves in the advancing direction V.

If the drive member 5 is operated by exerting a pressure force on a triggering element 16 in the advancing direction V, the drive member 5 and the coupler input member 6 together complete an axial coupler stroke of length X. In this drive stroke movement or coupler movement, the coupler input member 6 pushes the coupler intermediate member 7 in the advancing direction V, against the restoring elasticity force of the restoring member 10. In the course of the stroke movement, the engaging elements 6*a* and 8*a* pass into engagement with each other, while the coupler intermediate member 7 simultaneously moves relative to the decoupling member 11 until it passes out of the rotationally secured engagement with the decoupling member 11. The coupler intermediate member 7 remains in the rotationally secured engagement with the coupler sleeve 8. The coupler movement is limited by a stopper of the triggering element 16 on the coupler sleeve 8; in the exemplary embodiment, on its proximal facing area (FIG. 3).

FIG. 5 shows the injection apparatus in the coupled state. The engaging elements 6*a* and 8*a* are axially superimposed, such that the coupler engagement is established as a rotationally secured engagement between the coupler input member 6 and the coupler sleeve 8. The engagement between the coupler intermediate member 7 and the decoupling member 11 is not released until the coupler engagement is securely established.

For setting the dosage, a user rotates the dosing member 18, which locks in easily releasable locking positions. The dosing member 18 is connected to the coupler input member 6 such that it is secured against rotating and also cannot be moved axially, such that the latter rotates with it. The drive member 5 guided linearly in and counter to the advancing direction V at 4*b* is moved, by the dosing movement of the coupler input member 6, in the proximal direction and then protrudes out of the casing part 4. The axial dosing path of the drive member 5 follows from the rotational angle by which the dosing member 18 is rotated and the thread pitch in the threaded engagement between the drive member 5 and the coupler input member 6 which abuts against the coupler intermediate member 7 in the advancing direction V and against the casing part 4 counter to the advancing direction V.

Figures 6, 7:
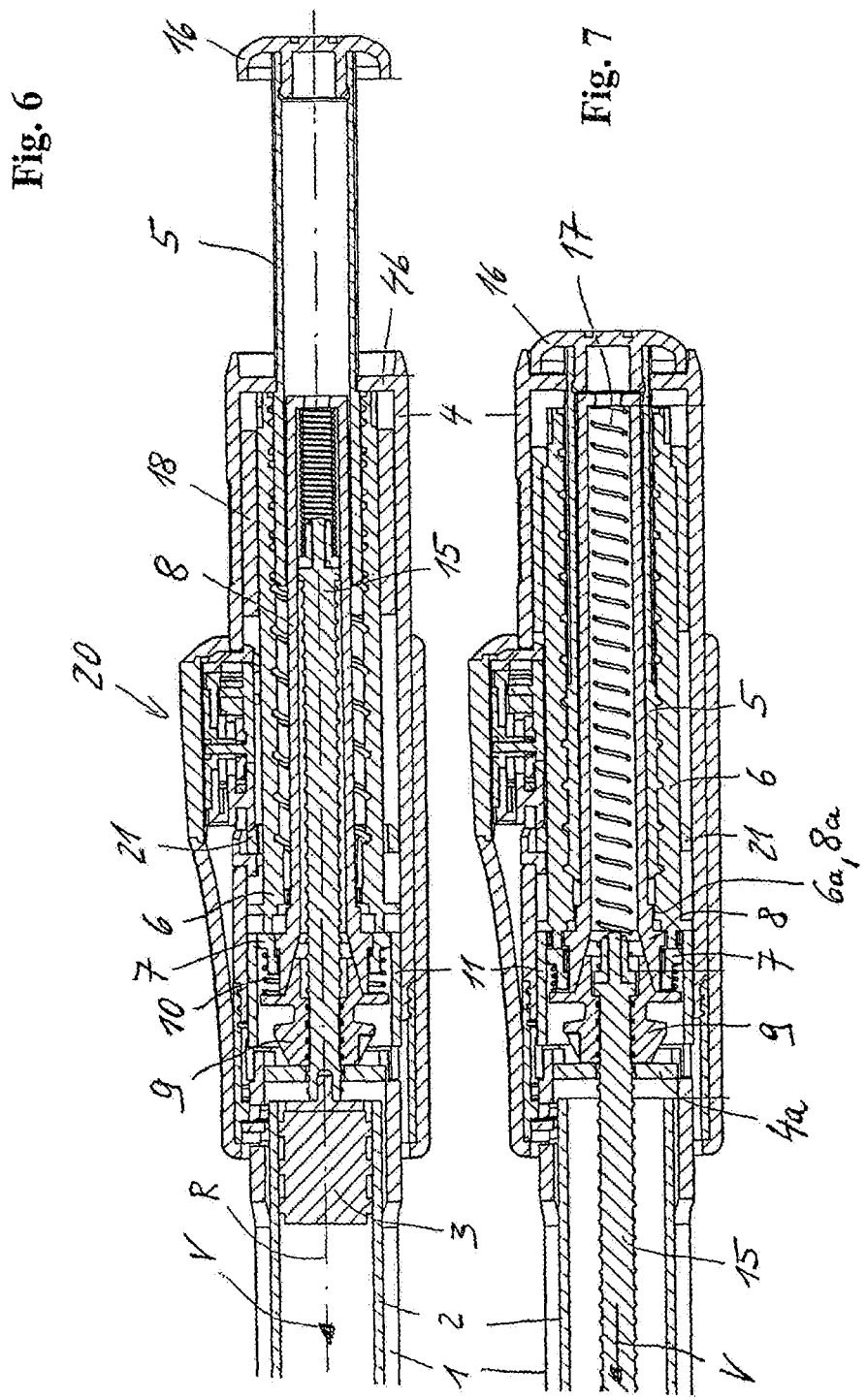
FIG. 6 shows the injection apparatus of FIG. 1 after a dosage has been set.
FIG. 7 shows the injection apparatus of FIG. 1 after a reservoir has been emptied.

FIG. 6 shows the injection apparatus with the container 2 still completely filled, after a first dosage has been set or selected. In this state, the user penetrates the skin with the injection needle, for a subcutaneous injection. Once the injection needle has been placed, the user operates the drive member 5 by pressing it in the advancing direction V, into the casing part 4. In the first portion of the drive movement, coupler movement or coupler stroke X, the drive member 5 slaves the coupler input member 6, against the elastic restoring force of the restoring member 10, until the coupler engagement with the coupler sleeve 8 is established and the rotationally secured engagement between the coupler intermediate member 7 and the decoupling member 11 is released. As soon as the coupler sleeve 8 and together with it the coupler output member 9 can freely rotate about the common threaded axis R, the coupler stroke X is complete and a delivery stroke follows as the second portion of the drive movement. During the delivery stroke, the drive member 5 is pressed further in the advancing direction V. Since the coupler input member 6 cannot perform any further movement in the advancing direction V once it abuts axially against the coupler intermediate member 7, it rotates—in the threaded engagement with the drive member 5 which is guided such that it is secured against rotating—about the common threaded axis R. When rotated in the coupler engagement, the coupler input member 6 slaves the coupler sleeve 8, which slaves the coupler output member 9. The coupler sleeve 8 is held in the casing part 4, together with the coupler output member 9, such that it cannot be moved axially. The rotational movement of the coupler output member 9 advances the piston rod 15, via the threaded engagement with the piston rod 15 and its rotationally secured linear guide at 4*a*, and thus causes the delivery movement of the piston rod 15 and together with it the piston 3. As soon as the injection button 16 passes into abutting contact against the coupler sleeve 8 in the course of the drive and delivery movement (FIG. 3), the delivery process is complete.

If the user takes the pressure off the triggering element 16, then the restoring member 10 moves the coupler input member 6, via the coupler intermediate member 7, back to the holding position retracted out of the coupler engagement, as shown in FIGS. 2 and 4. The coupler input member 6 and together with it the drive member 5, the dosing member 18 and the dosage display 20, are decoupled from the coupler output member 9 and thus from the piston rod 15 by the retracting movement of the coupler input member 6. On the other hand, the piston rod 15 is again connected to the casing part 4, such that it is secured against rotating, via the returning coupler intermediate member 7 and decoupling member 11.

FIG. 7 shows the injection apparatus at the end of a final delivery which has emptied the container 2.

For exchanging the emptied container 2, the casing part 1 is detached from the casing part 4, e.g., by a unscrewing movement. When the casing parts 1 and 4 are detached, the decoupling member 11 is automatically moved relative to the casing part 4, counter to the direction of the coupler movement of the coupler input member 6 and counter to the advancing direction V. The casing part 4 mounts or carries the decoupling member 11 accordingly. The axial path which the decoupling member 11 thus travels relative to the casing part 4 is as long as the coupler stroke X, such that once the casing parts 1 and 4 have been detached, the decoupling member 11 lying axially opposite the coupler input member 6 blocks it, and the coupler input member 6 can no longer be moved in the advancing direction V, at least not into the coupler engagement with the coupler sleeve 8. Blocking the coupler input member 6 in the disengaged position prevents the coupler output member 9 from being able to pass into a rotationally secured connection with the casing part 4 and so prevent the piston rod 15 from retracting. In other words, it ensures that the piston rod 15 can be retracted into the casing part 4, without being blocked.

Figures 8, 9, 10:
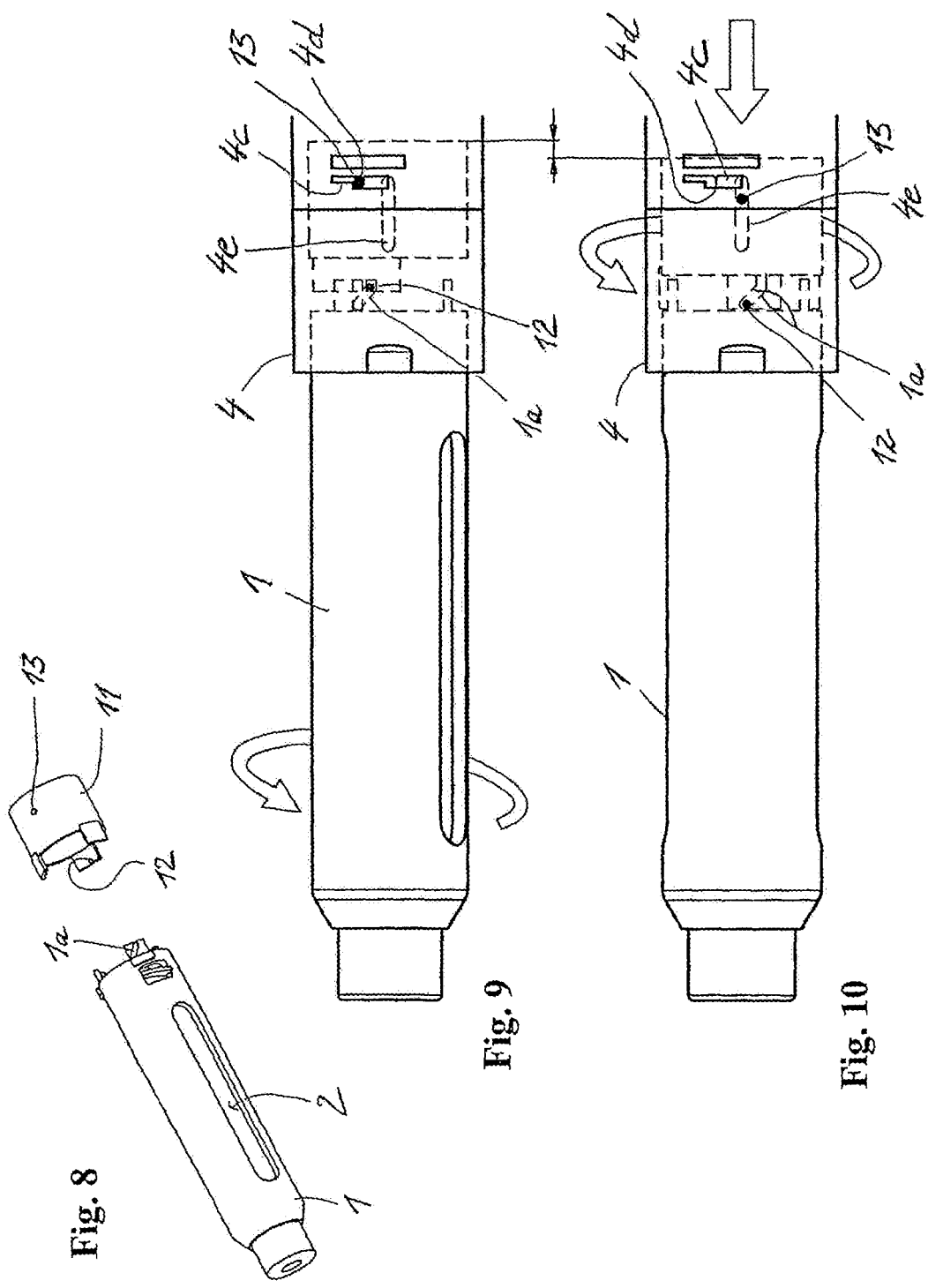
FIG. 8 shows a decoupling member and a casing part of the injection apparatus of FIG. 1.
FIG. 9 shows a distal portion of the injection apparatus of FIG. 1 with the casing parts connected.
FIG. 10 shows the distal portion while the casing parts are being detached.

FIG. 8 shows the decoupling member 11 and the first casing part 1 in a perspective view. The decoupling member 11 is a sleeve part and comprises, in a distal portion, three engaging elements 12 protruding radially inwardly and, in a proximal portion, a fixing element 13 protruding radially outwardly.

FIG. 9 shows the casing part 1 and a connecting portion of the casing part 4, wherein the hidden decoupling member 11 is shown by a broken line. For its decoupling function, the decoupling member 11 is accommodated in the connecting portion of the casing part 4 such that it can be rotated and moved axially. Its relative mobility is determined by an axial guide 4*c* and a circumferential guide 4*c*, along which the fixing element 13 moves in succession when the casing part 1 is detached from the casing part 4. The circumferential guide 4*c* extends at a right angle to the axial guide 4*e*, in the circumferential direction about the screw axis. It is formed as a breach or cavity in the casing part 4.

The decoupling member 11 is in a guiding engagement with the casing part 1. For the guiding engagement, one guiding curve 1*a* per engaging element 12 is formed on a shell outer area of the casing part 1 and guides the engaging element 12 and, thus, the decoupling member 11 when the casing parts 1 and 4 are detached. Another guiding curve 1*a*, spaced in parallel, guides the decoupling member 11 accordingly, when the casing parts 1 and 4 are connected (FIG. 10). In a distal portion, the guiding curve 1*a* runs obliquely, i.e. at a pitch, with respect to the screw axis of the screw connection between the casing parts 1 and 4, such that in the relative rotation between the casing parts 1 and 4 required for detaching them, the engaging element 12 performs an axial movement of the decoupling member 11 relative to the casing part 4 counter to the advancing direction V, sliding along the guiding curve 1*a*, until the fixing element 13 reaches the axial height of the circumferential guide 4*c*. The pitch measures about 45° and is constant. In principle, it can be selected from the entire range larger than 0° and smaller than 180° and, as applicable, can also be variable, as long as the relative movement required for detaching the casing parts 1 and 4 causes a movement of the decoupling member counter to the coupler movement X to be performed by the coupler input member for coupling.

A distal portion of the guiding curve 1*a* runs axially, such that when the casing parts 1 and 4 are screwed further apart, the fixing element 13 is moved along the circumferential guide 4*c*. In the course of this relative circumferential movement between the decoupling member 11 and the casing part 4, the fixing element 13 slides over a fixing element 4*d* in the region of the circumferential guide 4*c*. The fixing element 4*d* is formed as a cam on a strip portion of the casing part 4. The strip portion acts as a spiral spring which is fixedly clamped on both sides and elastically gives when the fixing element 13 moves over the fixing element 4*d*, to then spring back again into its initial position and form a releasable locking engagement for the decoupling member 11. In the locking position, the fixing element 13 abuts fixing element 4*d* in one circumferential direction and in the other circumferential direction abuts a collar formed in the circumferential guide 4*c* and is thus fixed in both circumferential directions.

FIG. 10 shows the two casing parts 1 and 4 and the decoupling member 11, after its fixing element 13 has been moved behind the fixing element 4*d* of the casing part 4. The decoupling member 11 is in the releasable locking engagement with the casing part 4 via the fixing elements 4*d* and 13 and in this way is axially fixed on the casing part 4 such that it is secured against rotating. In the locking position shown in FIG. 10, the decoupling member 11 blocks the coupler input member 6 and thus ensures that the drive member 5 and the piston rod 15 are decoupled. As soon as the decoupling member 11 has reached the locking position, its engaging element 12 moves out of the guiding engagement with the guiding curve 1*a* when the casing parts 1 and 4 are screwed further apart. The guiding curve 1*a* is shaped accordingly.

When the casing parts 1 and 4 are screwed together again, they are centred with respect to the circumferential direction by co-operating centering elements, such that the engaging element 12 of the decoupling member 11 passes into engagement with the guiding curve 1*a* again. As soon as the guiding engagement has been established, further screwing together automatically moves the decoupling member 11 out of the locking engagement of the fixing elements 4*d* and 13 until it again assumes the same position relative to the casing part 4 as in FIG. 9 and FIGS. 2 to 7. This corresponds to the operational position of the decoupling member 11.

While or before screwing together, the piston rod 15 is simply retracted into the casing part 4, which—due to the released coupler engagement, causes a rotational movement of the coupler output member 9.

The dosage display 20 of the first exemplary embodiment is coupled to the drive member 5 via a display coupling member 21 and the coupler input member 6. The display coupling member 21 is connected to the coupler input member 6 such that it is secured against rotating, by being able to move on the coupler member 6 relative to it in and counter to the direction of the coupler movement X, forming a ring in the exemplary embodiment. Conversely, the display coupling member 21 can be rotated with respect to the casing part 4 about the rotational axis R, but is held such that it cannot be moved axially relative to the casing part 4. The display coupling member 21 circumferentially comprises teeth, which in the exemplary embodiment are conical, via which it is in toothed engagement with a gear of the dosage display 20 to introduce the dosing movement and also the drive movement into the gear.

FIGS. 11-18 show an injection apparatus of another exemplary embodiment of the present invention. The injection apparatus exhibits some modifications with regard to the coupling and decoupling of the drive member 5 and piston rod 15. The drive member 5 and the piston rod 15 themselves, and how they co-operate in principle when coupling and decoupling, may remain the same. Functionally identical components are provided with the same reference numbers as in the first exemplary embodiment, and, to indicate modifications the relevant components are provided with the same reference numbers, but apostrophised.

Figures 11, 12:
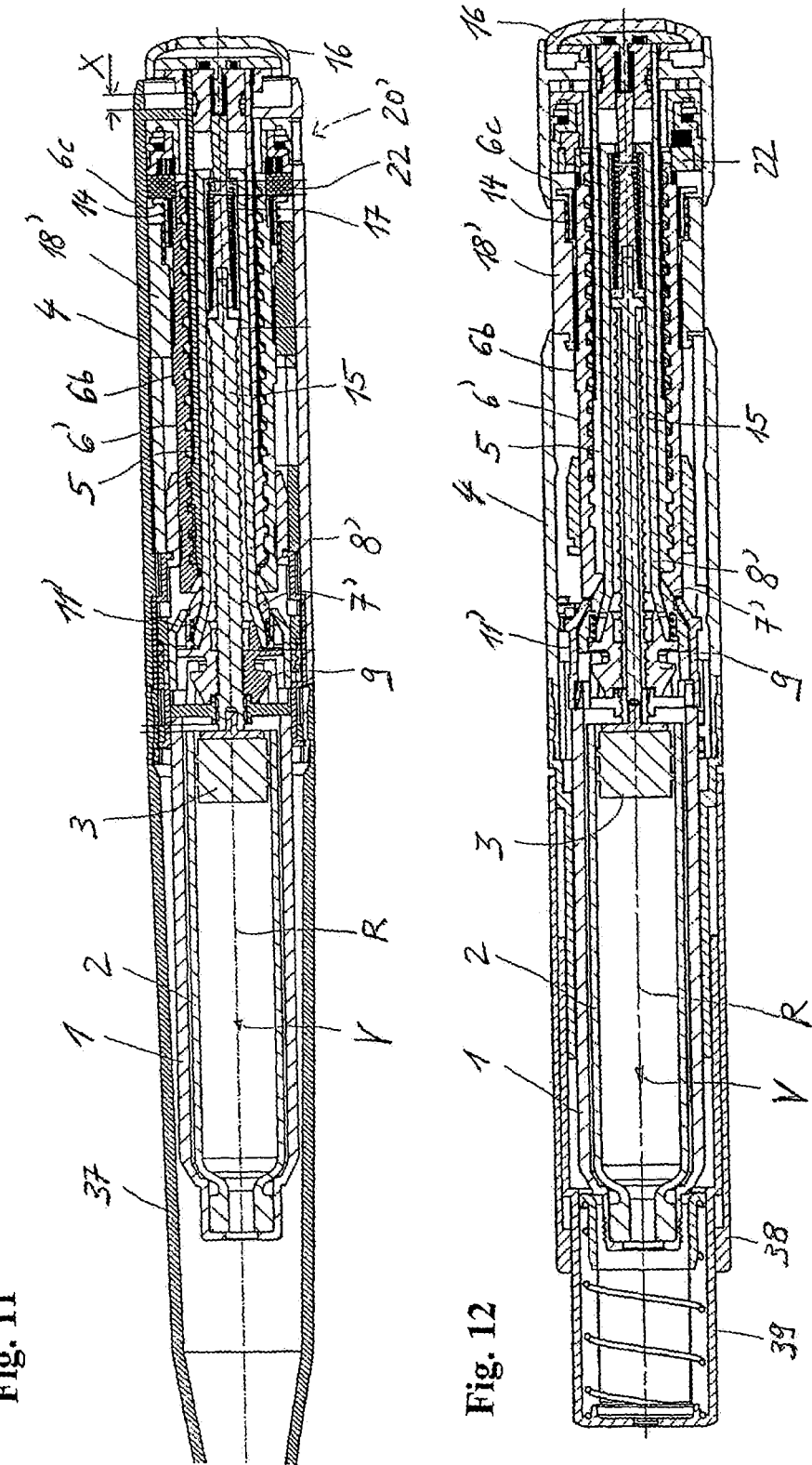
FIG. 11 shows, in a longitudinal section, another exemplary injection apparatus, with the coupler open.
FIG. 12 shows the injection apparatus of FIG. 11, with the coupler closed, in a different longitudinal section.

FIG. 11 shows the injection apparatus in its resting state, in which the drive member 5 is decoupled from the piston rod 15. The first casing part 1 is covered by a protective cap 37 which is connected to the casing part 4 and removed for administering the product. Unlike the first embodiment, the coupler engagement is established and released between the modified coupler input member 6' and the modified coupler intermediate member 7'.

FIG. 12 shows the injection apparatus of the second embodiment in its coupled state, which is established by charging the triggering element 16, and therefore the drive member 5 and the coupler input member 6', with a drive force acting in the advancing direction V. However, as in corresponding FIG. 3 of the first embodiment above, no dosage has yet been selected or only a small dosage of a few units for priming. The protective cap 37 has been replaced by a casing part 38 which is placed onto the casing part 4 and snapped onto it. The casing part 38 mounts or carries a needle protection 39, e.g., in the form of a needle protecting sleeve, such that it can be elastically moved counter to the advancing direction V. When the injection needle (not shown) is injected, the needle protection 39 springs counter to the advancing direction V, into the casing part 38. In a reversal of this movement, the needle penetrates through a distal opening of the needle protection 39.

Figures 13, 14, 18:
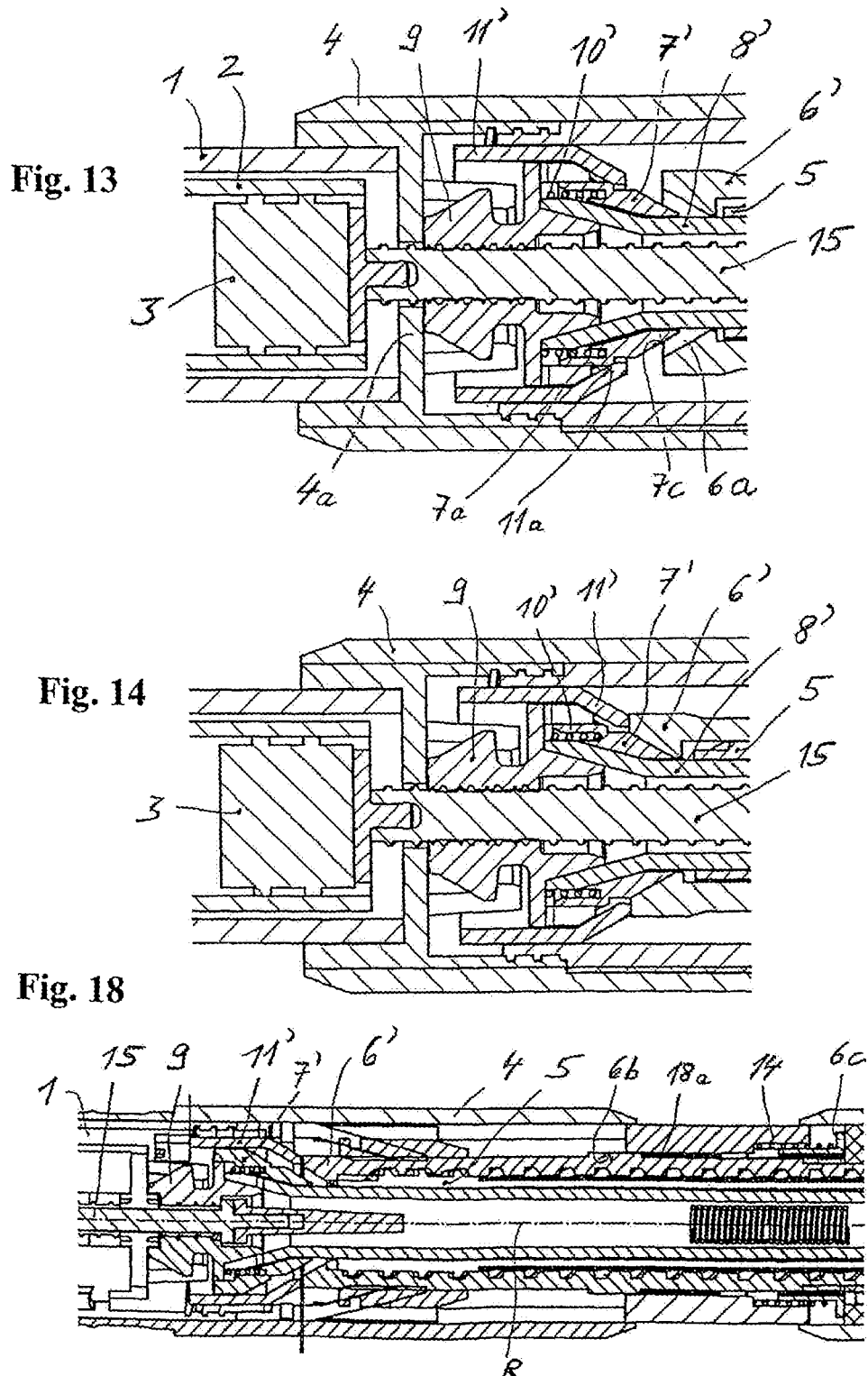
FIG. 13 shows a detail from FIG. 11.
FIG. 14 shows a detail from FIG. 12.
FIG. 18 shows a detail from FIG. 17.

FIGS. 13 and 14 show the region of the coupler engagement in detail, wherein FIG. 13 shows for the decoupled state and FIG. 14 shows for the coupled state. Unlike the first embodiment, the engaging elements 6*a* and 7*c* between which the coupler engagement is established exhibit an inclination with respect to the advancing direction V. The engaging elements 6*a* and 7*c* are each formed in the manner of a conical toothed ring encircling the threaded axis of the piston rod 15, wherein the coupler input member 6' forms its engaging elements 6*a* on its distal end as an inner cone, and the coupler intermediate member 7' forms the engaging elements 7*c* on its proximal end as an outer cone. The conical engaging areas are congruent to each other and lie directly opposite each other, axially facing, with the clear distance X. Instead of being conical, the coupler areas could also be otherwise suitably shaped, e.g., congruently convex/concave.

The coupler intermediate member 7' can be moved axially and is in engagement with the coupler output member 9, such that it is secured against rotating, in any axial position. It is again formed as a sleeve part and mounted on the coupler output member 9 such that it can be slid axially. For this purpose, it penetrates through the coupler sleeve 8' which is axially slit accordingly, which however is not visible in the figures. The rotationally secured connection is created in a positive lock via engaging elements formed as axially linear teeth. The restoring member 10', which is the same in its embodiment and installation but reduced with regard to its function, is tensed between the coupler output member 9 and the coupler intermediate member 7', as in the first embodiment, and charges the latter with an elasticity force, counter to the advancing direction V.

In the decoupled state, in which the coupler input member 6' is retracted from the coupler intermediate member 7' counter to the advancing direction V, as shown in FIG. 13, the restoring member 10' presses the coupler intermediate member 7' into the rotationally secured engagement with the decoupling member 11'. The corresponding engaging elements are again indicated as 7*a* and 11*a*. The engaging elements 7*a* and 11*a* are also formed as conical toothed rings. The engagement between the coupler intermediate member 7' and the decoupling member 11' can alternatively be in a purely frictional lock. In this case, the engaging elements 7*a* and 11*a* comprise mutually facing congruent frictional areas which could be mutually facing conical areas.

Another modification exists in the dosing member 18'. Unlike the dosing member 18 of the first embodiment, the dosing member 18' cannot be moved relative to the casing part 4 in the direction of the coupler movement X. Instead, the coupler input member 6' is again connected to the dosing member 18' such that it is secured against rotating, but such that it can be moved axially. The rotationally secured engagement between the coupler input member 6' and the dosing member 18' exists in the decoupled state of the drive member 5 and the piston rod 15 and is released in the course of the coupler stroke X, namely directly before the rotationally secured connection between the coupler output member 9 and the casing part 4 is released. For this engagement, the coupler input member 6' and the dosing member 18' are provided with engaging elements 6*b* and 18*a* which are formed on shell areas, radially facing each other, of the two members 6' and 18' in the manner of grooves and springs. With respect to the rotationally secured connection between the coupler input member 6' and the dosing member 18', reference may also be made to FIGS. 11 and 12. The rotationally secured connection exists in the decoupled state shown in FIG. 11, and is released in the coupled state shown in FIG. 12.

Another difference with respect to the first embodiment exists with regard to the holding means. In the second embodiment, the restoring member 10' has no effect which separates the coupler members 6' and 9 from each other. The holding means of the second embodiment includes a restoring member 14, a supporting structure 6c and the dosing member 18'. The restoring member 14 charges the coupler input member 6', via the supporting structure 6c, with an elastic restoring force which counteracts the coupler movement X of the coupler input member 6'. In the direction of the coupler movement X, which coincides with the advancing direction V, the restoring member 14 is supported on the dosing member 18' which forms a supporting collar for this purpose. The supporting structure 6c is connected to the coupler input member 6' such that it cannot be moved in or counter to the direction of the coupler movement X. It is formed as a short sleeve with an outer flange on which the restoring member 14 is supported. Counter to the direction of the coupler movement X, the supporting structure 6c abuts with respect to the casing part 4. The coupler movement X moves the coupler input member 6', against the elastic restoring force of the restoring member 14, into the coupler engagement with the coupler intermediate member 7'. As in the first embodiment, the restoring member 14 is formed as a pressure spring charged with a pressure force in the direction of the coupler movement X.

The mode of operation of the modified coupler (comprising components 6'-11' and 14') is the same as the coupler of the first embodiment. Thus, in the decoupled state, the coupler output member 9 is connected, such that it is secured against rotating, to the casing part 4 via the coupler sleeve 8', the coupler intermediate member 7' and the decoupling member 11'. Operating the injection button 16 and consequently performing the coupler stroke X (FIG. 11) establishes the coupler engagement, in the second embodiment between the coupler input member 6' and the coupler intermediate member 7'. In the first phase of the coupler stroke X, the engaging elements 6a and 7c interlock with each other, such that the coupler input member 6' is connected, such that it is secured against rotating, to the coupler output member 9 via the coupler intermediate member 7' and the coupler sleeve 8'. Only once the rotationally secured engagement has been established is the coupler intermediate member 7' moved out of engagement with the decoupling member 11' by the coupler input member 6' pressing in the advancing direction V, such that the coupler output member 9 can freely rotate about the threaded axis R formed with the piston rod 15 and the coupler engagement is completely established.

Figures 15, 16, 17:
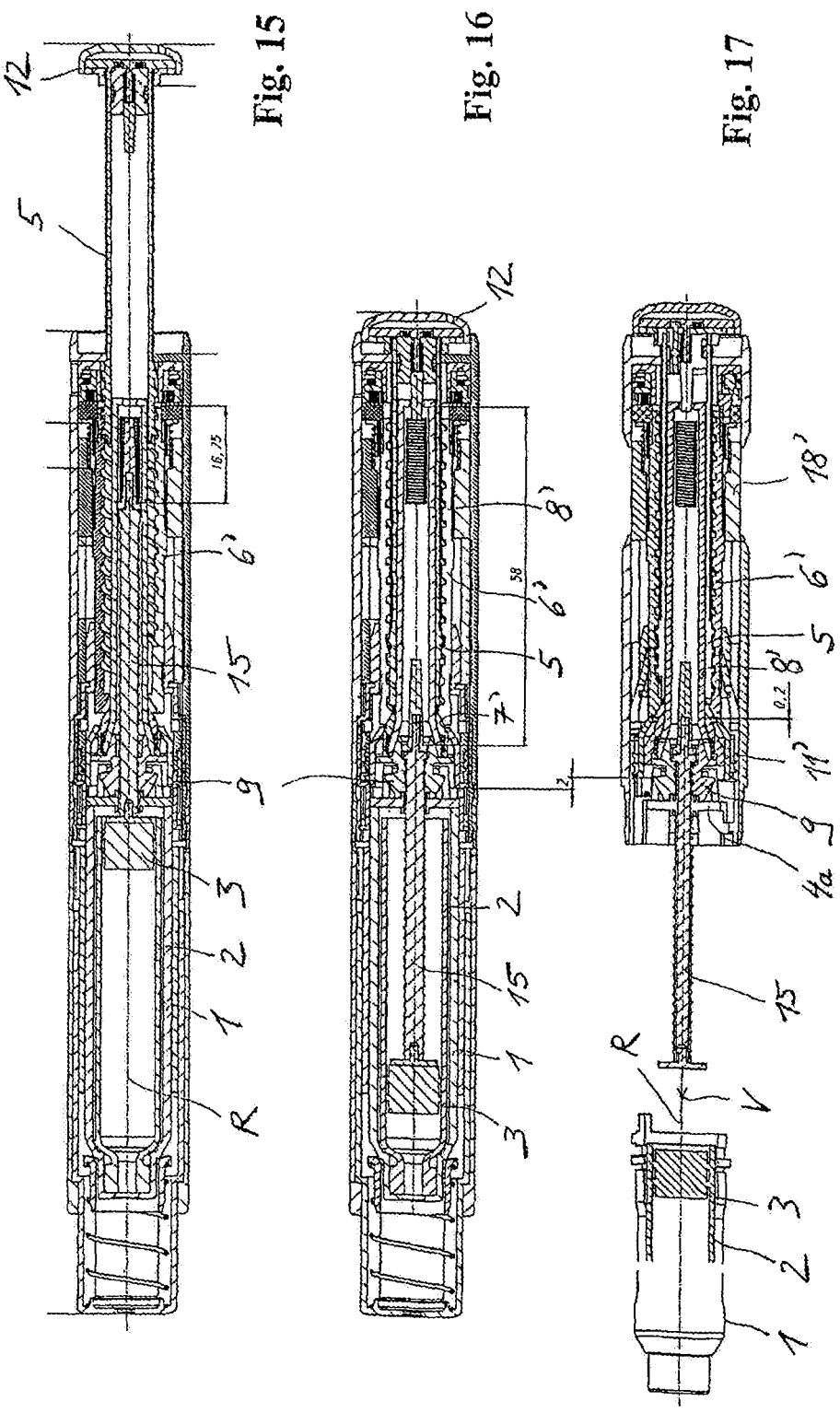
FIG. 15 shows the injection apparatus of FIG. 11, after a dosage has been set.
FIG. 16 shows the injection apparatus of FIG. 11, after the reservoir has been emptied.
FIG. 17 shows the injection apparatus of FIG. 11, with the casing parts detached from each other.

FIG. 14 shows the injection apparatus in its coupled state, i.e. in the coupler engagement. FIGS. 15 and 16 correspond to FIGS. 6 and 7 of the first exemplary embodiment, such that cross-reference can be made.

FIG. 17 shows the injection apparatus of the second embodiment while the reservoir 2 is being exchanged. Once the reservoir 2 has been emptied, as shown in FIG. 16, the casing part 1 is detached from the casing part 4, which moves the decoupling member 11' into the decoupling position. This function fully corresponds to that of the decoupling member 11 of the first embodiment, such that reference can be made to the explanations in that embodiment and to FIGS. 8-10.

In the state shown in FIG. 17, the casing part 1 is already accommodating the new reservoir 2. To connect the casing part 1 to the casing part 4, the casing part 1 can be moved towards the casing part 4 using the piston 3 which proximally seals the reservoir 2. The piston rod 15 which freely protrudes out of the casing part 4 is moved back by the pressing piston 3 in the threaded engagement with the coupler output member 9 which can be freely rotated but is axially fixed. Due to the rotationally secured linear guide 4a, which in the second embodiment is formed by a coupler receptacle which is inserted into the casing part 4 such that it is secured against rotating, the piston rod 15 completes an axial linear movement when retracted, while the coupler output member 9 freely rotates, together with the coupler sleeve 8', about the common threaded axis. Instead of moving the piston rod 15 back, pressing against the piston 3, the piston rod 15 can also be moved back beforehand by pressing directly on its plunger.

FIG. 18 shows the coupler region, with the decoupling member 11' situated in the decoupling position, in detail. The function of the decoupling member 11' corresponds to that of the first embodiment, namely blocking the coupler input member 6' in the retracted axial position.

The dosing movement and the drive movement are also introduced into a gear of the dosage display 20' via the coupler input member 6' and a display coupling member 22 in the second embodiment. The display coupling member 22 is also connected to the coupler input member 6', such that it is secured against rotating, and cannot be moved relative to the casing part 4 in and counter to the direction of the coupler movement X.

FIGS. 19-24 show another exemplary embodiment of an injection apparatus in accordance with the present invention in which, during administering, the drive force for delivering the product is not applied manually but rather by a drive member 25 formed as a drive spring. The drive member 25 is tensed by setting the dosage to be administered. The spring energy absorbed when setting the dosage is released when the apparatus is triggered and converted into advancing the piston rod 15.

Figure 19:
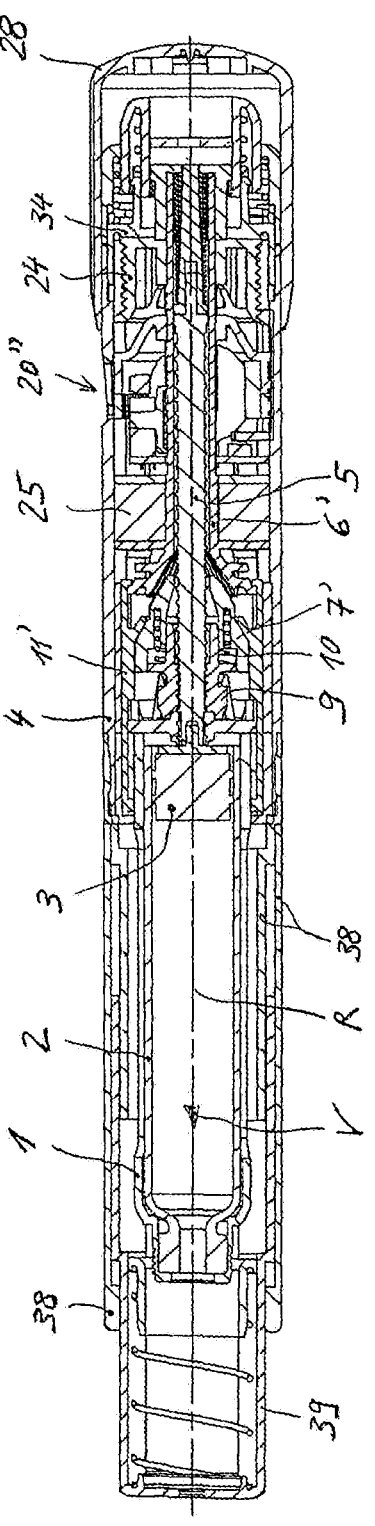
FIG. 19 an injection device of another exemplary embodiment of the present invention.

FIG. 19 shows the injection apparatus with the assembled casing part 38 and the needle protection 39 accommodated in it such that it can be slid counter to the advancing direction V, against the force of a restoring spring.

Figures 20, 21:
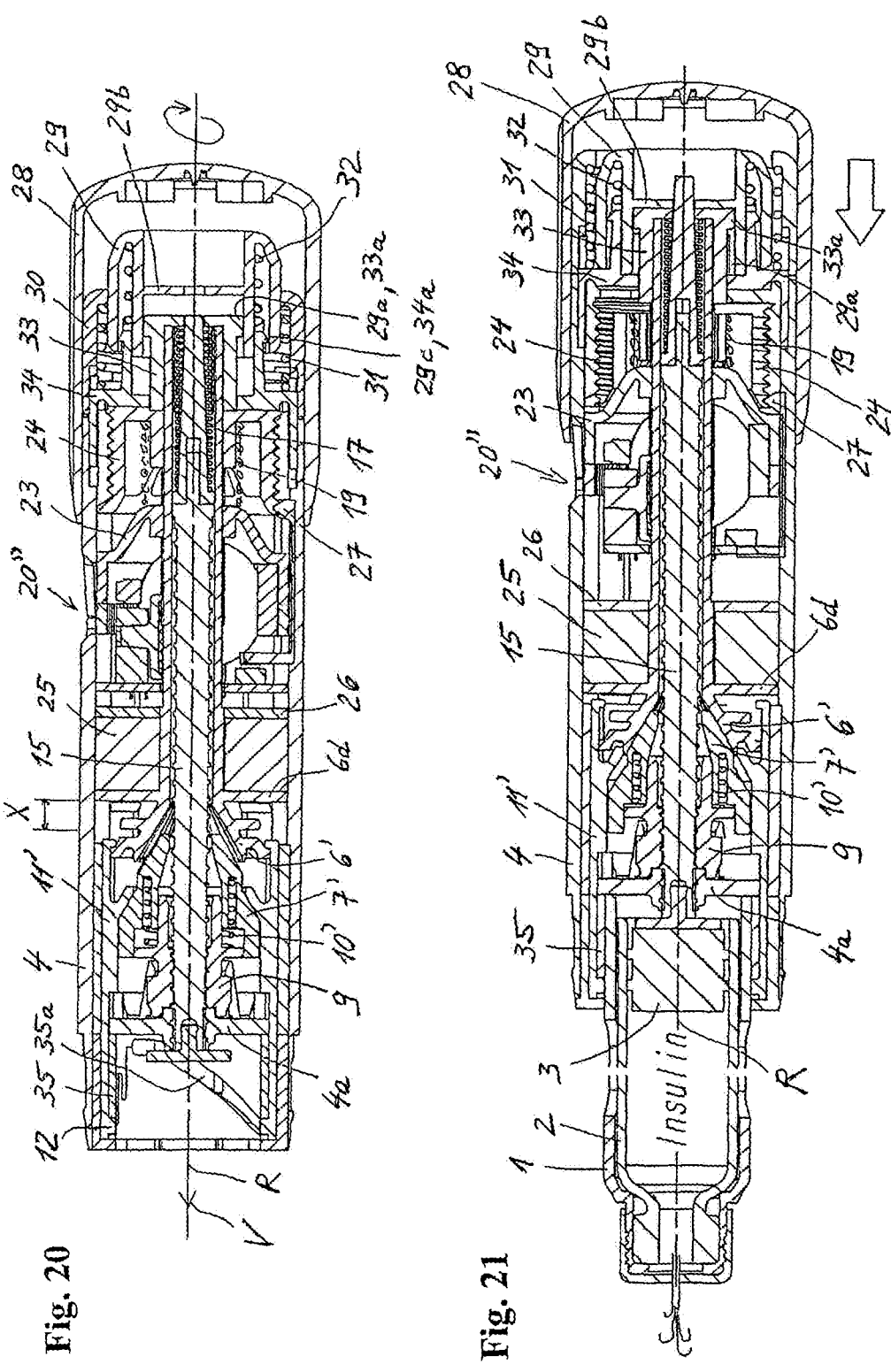
FIG. 20 a proximal part of the injection device of FIG. 19, with the coupler open.
FIG. 21 the injection device of FIG. 19, with the coupler closed.

FIGS. 20 and 21 show the casing part 4 with the operational and other components of the injection apparatus accommodated in it. In FIG. 20 it is in a resting state, comparable to the preceding embodiments, in which the dosage can be set and, in FIG. 21, it is in the coupler engagement. Unless stated differently below, reference is made in particular to FIGS. 20 and 21.

The drive member 25 is a spiral spring acting as a torsion spring, comprising spring windings which encircle the threaded axis R of the threaded engagement between the coupler output member 9 and the piston rod 15. The spring windings are arranged one over the other, radially with respect to the threaded axis R; they exhibit a zero pitch with respect to the threaded axis. An inner end of the spring windings is fastened to the coupler input member 6', and an outer end is fastened to a supporting structure 26 which is connected to the casing part 4 such that it can be moved in the direction of the coupler movement X but is secured against rotating. On the other hand, the supporting structure 26 is connected to the coupler input member 6' such that it cannot be moved in and counter to the direction of the coupler movement X. The coupler input member 6' can be rotated about the threaded axis R relative to the supporting structure 26. Another supporting structure 6d is connected to the coupler input member 6' such that it cannot be moved in and counter to the direction of the coupler movement X. The coupler input member 6' and the supporting structure 6d may be formed integrally. The drive member 25 is axially enclosed by the supporting structures 6*d* and 26.

The functionality of the coupler corresponds generally to that of the second embodiment, such that the same reference signs are used for the coupler members 6'-10' and the decoupling member 11'. Unlike the coupler of the second embodiment, however, the coupler sleeve 8' in that embodiment has been omitted. The coupler intermediate member 7' is directly in an engagement with the coupler output member 9 which transfers the rotational drive movement of the coupler input member 6' onto the coupler output member 9.

A dosage display 20" is coupled to the coupler input member 6' via a display coupling member 23. Like the display coupling members 21 and 22 of the other embodiments above, the display 20" is connected to the coupler input member 6', such that it is secured against rotating. The display coupling member 23 cannot be moved in and counter to the direction of the coupler movement X relative to the casing part 4. As in the first and second embodiments described above, the rotationally secured connection of the display coupling member 23 exists both in the decoupled and in the coupled state of the device.

For setting the dosage and during storage, to prevent the coupler input member 6' from the rotational drive movement and to hold the drive member 25 in its tensed state, a rotational block or lock is formed between the coupler casing 6' and the casing part 4. In the holding position of the coupler members 6', 7' and 9 shown, the rotational block exists between a first blocking member 24 and a second blocking member 34. The blocking member 24 is connected to the coupler input member 6', such that it is secured against rotating. The blocking member 34 is connected to the casing part 4, such that it is secured against rotating but can be moved in and counter to the direction of the coupler movement X relative to the casing part 4 and the coupler input member 6'. The facing areas of the blocking members 24 and 34, which contact each other in the blocking engagement, form a ratchet which allows a rotational movement of the coupler input member 6' which tenses the drive member 25, and prevents a rotational movement in the opposite direction.

Figure 23:
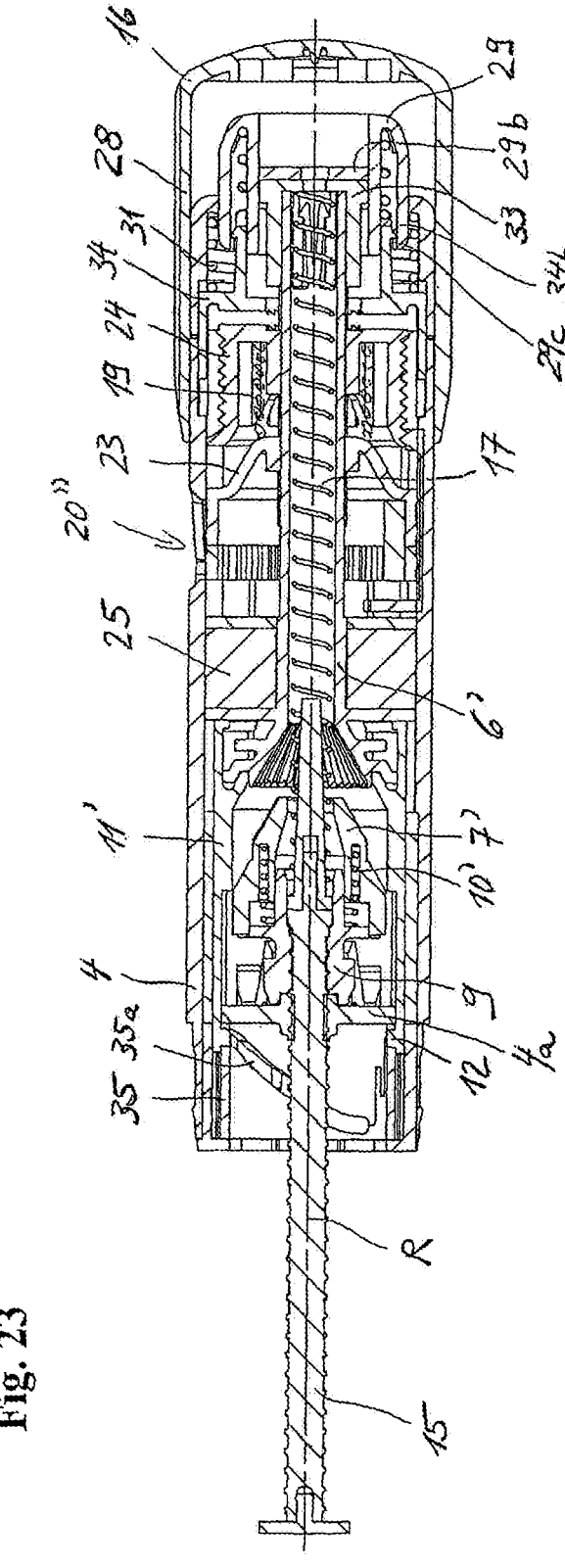
FIG. 23 the proximal part of the injection device of FIG. 19, after the reservoir has been emptied.
Figure 24:
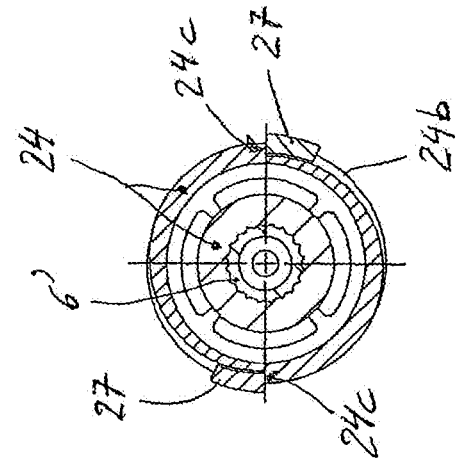
FIG. 24 a blocking member and a stopping member of the injection device of FIG. 19.
Figure 24:
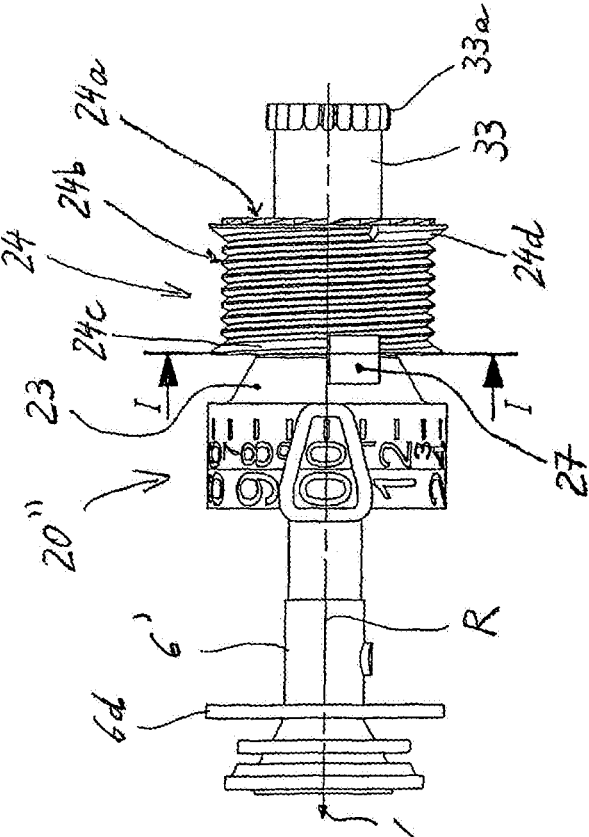

FIG. 24 shows the coupler input member 6' together with the blocking member 24 mounted on it, such that it is secured against rotating, the display coupling member 23 connected to the coupler input member 6', such that it is secured against rotating, and a connecting part 33 connected to the input member 6' such that it cannot be moved. The display coupling member 23 forms a units counting ring of the dosage display 20" and is suitably coupled to a tens counting ring to display the dosage set. On a proximal facing side facing the blocking member 34, the blocking member 24 is provided with blocking teeth 24*a* which are arranged evenly about the axis R and, in the blocking engagement, co-operate with counter teeth of the blocking member 34, to form the rotational block with respect to the drive movement. For a second function connected with dosing and delivery, a shell outer area of the blocking member 24 is provided with a thread 24*b*, the threaded axis of which coincides with the threaded axis R of the piston rod 15. A stopping member 27 engages with the thread 24*b*. The stopping member 27 is guided such that it can be linearly moved parallel to the threaded axis R, in the exemplary embodiment, in an axial groove on the inner shell area of the casing part 4. The blocking member 24 forms a rotational stopper 24*c* for the stopping member 27, which limits the drive movement of the coupler input member 6' which advances the piston rod 15. It forms another rotational stopper 24*d* for the stopping member 27, which determines the maximum dosage which can be delivered and set. Another stopping member 27 is arranged on the other side of the threaded axis R, opposite the stopping member 27 which can be seen in the view in FIG. 23, and co-operates in the same way with two other rotational stoppers 24*c* and 24*d*. The thread 24*d* is double-threaded. The stopping members 27 simultaneously abut against the respectively assigned rotational stoppers 24*c* and 24*d*, as can be seen in the cross-sectional representation in FIG. 23 for the rotational stoppers 24*c*. The rotational stoppers 24*c* determine a zero dosage position and the rotational stoppers 24*d* determine a maximum dosage position.

In the third embodiment, the holding means is formed in another variant. It includes a restoring member 19, as well as the display coupling member 23 and the blocking member 24. The restoring member 19 is supported on the casing part 4 via the display coupling member 23 in the direction of the coupler movement X and on the blocking member 24 counter to the direction of the coupler movement X. The restoring member 19 presses the blocking member 24 until it abuts against the connecting part 33. Since the connecting part 33 is connected to the coupler input member 6' such that it cannot be moved in and counter to the direction of the coupler movement X, the restoring member 19 thus exerts an elastic restoring force, acting counter to the direction of the coupler movement X, on the coupler input member 6' via the blocking member 24 and the connecting part 33, said elastic restoring force holding the coupler input member 6' in the holding position retracted out of the coupler engagement. It again acts as a pressure spring. The blocking member 24 is a sleeve part comprising an outer shell forming the thread 24*b*, an inner shell serving to mount it on the coupler input member 6' such that it is secured against rotating, and a base which connects the two shells and on which the blocking teeth 24*a* are formed. The restoring member 19 protrudes into the blocking member 24 which is cup-shaped in this way, and is supported on the base of the blocking member 24.

The restoring member 19 presses the blocking member 24 not only until it abuts against the connecting part 33, but also until it abuts against the casing part 4. Abutting in this other way prevents the blocking member 24 from being able to move counter to the direction of the coupler movement X beyond the holding position assumed in FIG. 20. The blocking member 24 can thus be moved relative to the coupler input member 6', against the restoring elasticity force of the restoring member 19, in the direction of the coupler movement X. Conversely, the coupler input member 6' can be moved counter to the direction of the coupler movement X relative to the blocking member 24 abutting against the casing part 4.

The equalizing spring 17, tensed between the piston rod 15 and the connecting part 33, supports the restoring member 19 in its function of holding the coupler input member 6' in the holding position. The equalizing spring 17 could in principle replace the restoring member 19 for retracting the coupler members 6', 7' and 9. It is weak enough that, at least once it has been partially relaxed, it can no longer hold the coupler members 6'-9 in the holding position, and thus can no longer hold the coupler in the decoupled state, with certainty.

A triggering element 28 is provided for triggering the drive member 25. The triggering element 28 can be moved translationally relative to the casing part 4 in the direction of the coupler movement X—in this embodiment, the advancing direction V and/or distal direction—and rotationally about the rotational axis R of the coupler input member 6', which coincides with the threaded axis R of the piston rod 15, and is guided in these two movements by the casing part 4. The translational movement in the distal direction establishes the coupler engagement between the coupler input member 6' and the coupler intermediate member 7' and releases the rotational block between the blocking members 24 and 34, which triggers the drive member 25, i.e. delivery. The translational movement in the advancing direction V is therefore also referred to in the following as the triggering movement.

In another function, the triggering element 28 forms the dosing member of the third embodiment. Via multiple intermediate members, the rotational movement of the triggering element 28 relative to the casing part 4 sets the product dosage which can be delivered by the next delivery process. This movement is also referred to in the following as the dosing movement. From the zero dosage position, which is shown in FIG. 20 and determined by the stopping members 27 abutting the rotational stoppers 29c of the blocking member 24 which limit the drive movement of the coupler input member 6', the dosage can be set by rotating the triggering element 28 in the direction of the rotational direction arrow indicated, the dosing direction. The rotational dosing movement of the triggering element 28 is transferred onto the coupler input member 6' via an inner part 29—which is connected to the triggering element 28 such that it is secured against rotating and shifting or is formed integrally with it—and the connecting part 33. For transferring, the inner part 29 and the connecting part 33 are in an engagement with each other, such that they are secured against rotating, and the connecting part 33 is connected to the coupler input member 6', such that it is secured against rotating. For securing against rotating, the inner part 29 and the connecting part 33 are provided with an inner teeth 29a and an outer teeth 33a which interlock with each other in the resting state of the apparatus and can be axially shifted with respect to each other.

The triggering element 28 is arranged in the proximal end region of the casing part 4 so as to be user-friendly. Its outer sleeve part surrounds the casing part 4. A base of the triggering element 28 forms a proximal end of the injection apparatus. For setting the dosage, the triggering element 28 can be operated as a turning button and is ribbed on its outer shell area for this purpose. For triggering, it can be operated as a push button. During the dosing movement, the triggering element 28 locks with the casing part 4 in discrete rotational angular positions corresponding to the dosage units.

A stopper element 29b facing a proximal facing area of the connecting part 33 projects radially inwards from the inner part 29. In the resting state of the apparatus, a clear distance remains between the connecting part 33 and the stopper element 29b, said clear distance being just large enough that the rotational block between the inner part 29 and the connecting part 33 is released during the triggering movement of the triggering element 28, before the stopper element 29b terminates the relative movement of the triggering element 28 relative to the connecting part 33 by an abutting contact.

The second blocking member 34 is tensed in the blocking engagement with the blocking member 24 by a blocking spring 31. For this purpose, the blocking spring 31 is supported in the direction of the coupler movement X on the blocking member 34 and counter to the coupler movement X on a casing part 30 which is fixedly connected to the casing part 4. Another spring 32, arranged between the inner part 29 and the blocking member 34, tenses the triggering element 28 relative to the blocking member 34 into a proximal end position. The blocking member 34 is axially guided, such that it is secured against rotating, by the casing part 4. The casing part 4 forms a distal and a proximal stopper for the mobility of the blocking member 34.

In the resting state shown in FIG. 20, the user sets the dosage by rotating the triggering element 28 in the dosing direction. During this rotational dosing movement, the triggering element 28 slaves the connecting part 33 via the rotational block 29a, 33a, and the connecting part 33 for its part slaves the coupler input member 6' which thus completes the same rotational dosing movement as the triggering element 28. Rotating the coupler input member 6' tenses the drive member 25. In engagement with the thread 24b of the blocking member 24, the stopping member 27 migrates from the stopper 24c of the thread 24b which determines the zero dosage, in the direction of the stopper 24d which determines the maximum dosage (FIG. 24).

Figure 22:
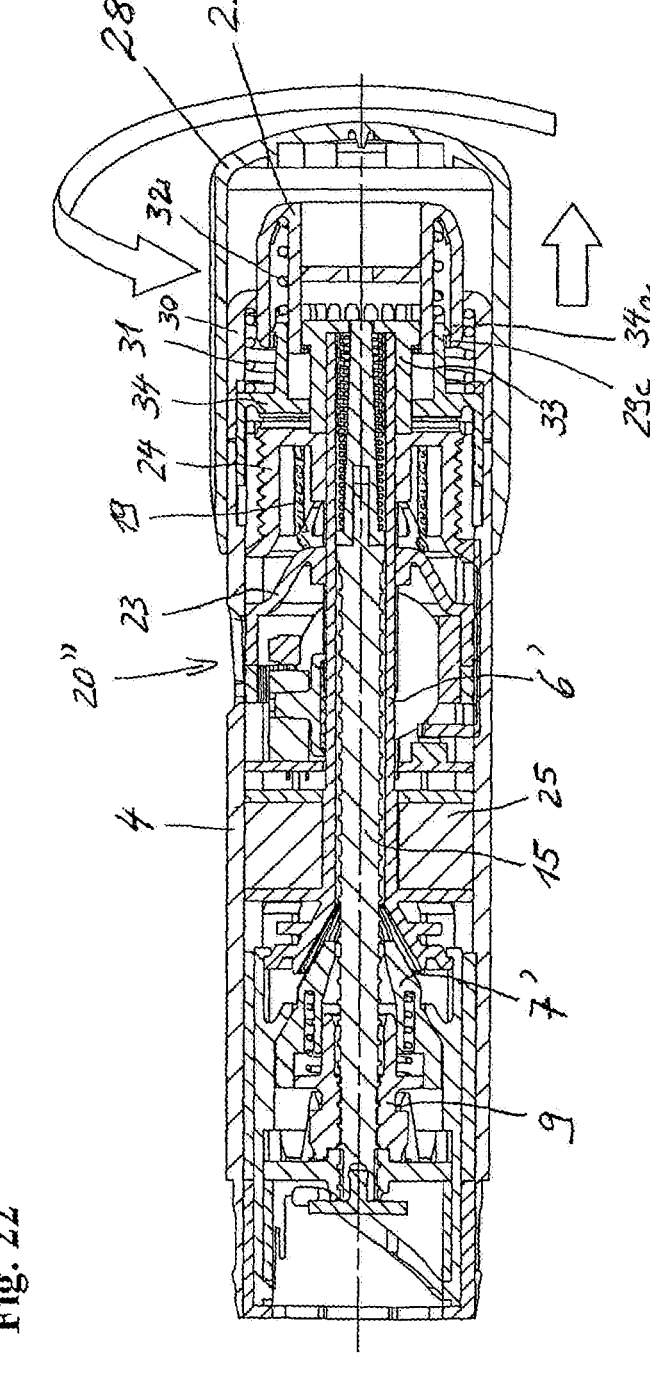
FIG. 22 the proximal part of the injection device of FIG. 19, when correcting the dosage.

The injection apparatus also offers a convenient way of correcting the dosage, as is clear from a comparison of FIGS. 20 and 22. If the user has inadvertently set too high a dosage, he/she can correct the dosage by rotating the coupler input member 6' back. For correcting the dosage, the user pulls the triggering element 28 in the proximal direction. This retracting movement of the triggering element 28 is indicated in FIG. 22 by an arrow, as is the rotational direction for correcting. In the resting state of the apparatus, the inner part 29 and the blocking member 34 are in a slaving engagement with respect to a movement in the proximal direction. The corresponding slaving elements are indicated as 29c and 34a. The slaving element 29c formed by the inner part 29 and the slaving element 34a formed by the blocking member 34 grip behind each other and form a latch for the retracting movement of the triggering element 28. Pulling on the triggering element 28 thus also moves the blocking member 34 in the proximal direction, against the force of the blocking spring 31, thus releasing it from the blocking engagement with the blocking member 24 which abuts against the casing part 4. As soon as the rotational block is released, the user can correct the dosage by means of a reverse rotational movement of the triggering element 28 and the still extant rotationally secured engagement between the inner part 29 and the connecting part 33. As soon as the user releases the triggering element 28, it snaps back in the distal direction together with the blocking member 34 due to the effect of the blocking spring 31, and the blocking member 34 thus snaps back into the blocking engagement with the blocking member 24. During the reverse rotational movement, the user expediently continues to hold the triggering element 28 fast, which is facilitated by the rotational angular locking positions of the triggering element 28. In principle, however, the user can also let it snap back and re-dose, as applicable.

Once the desired dosage has been set, the apparatus is placed onto the skin at the desired administering location, and the injection needle is injected. For injecting the needle, the triggering element 28 takes on another function, for which purpose it is coupled to the needle protection 39 (FIG. 19).

In a first phase of injecting, the user presses the injection apparatus against the skin, such that the needle protection 39 is moved in the distal direction relative to the casing part 38. However, this first part of the movement of the needle protection 39 does not yet expose the injection needle; rather, its tip remains short of the needle protection 39. In this first phase of the injecting process, the needle protection 39 abuts against a resisting element, such that it cannot be moved further in the distal direction relative to the casing part 38. While continuing to exert pressure on the injection apparatus in the direction of the skin, the user presses the triggering element 28 in the proximal direction. In the course of this first phase of its triggering movement, the triggering element 28 releases an abutting contact between the needle protection 39 and the resisting element, such that the injection apparatus, and together with it the injection needle, are moved relative to the needle protection 39 in the direction of the skin, and the injection needle injects. With respect to the function of the triggering element 28 for injecting the needle, reference may be made to the patent application entitled "Attachment Module for an Injection Device Comprising an Engagement Control for a Needle Covering Element" owned by the owner of the present application.

As soon as the injection needle has been subcutaneously placed, the drive member 25 can be released and the product delivered by pressing further onto the triggering element 28. In the second phase of the triggering movement of the triggering element 28, which follows the injection phase, the triggering element 28 and therefore the inner part 29 is pressed further in the distal direction relative to the connecting part 33, against the pressure of the spring 32, such that the rotational block (formed by components 29a, 33a) is released. The triggering element 28 can rotate idly. As soon as the rotational block has been released, the stopper element 29b passes into abutting contact with the connecting part 33. In the third phase of the triggering movement which then follows, the triggering element 28 presses the connecting part 33 and therefore the coupler input member 6' via the stopper element 29b, in the direction of the coupler movement X; in exemplary embodiments, in the advancing direction V. Due to the effect of the spring force of the blocking spring 31, the blocking member 34 follows this movement until it abuts against the casing part 4. Before the blocking member 34 reaches the abutting position, the coupler input member 6' passes into the coupler engagement with the coupler intermediate member 7'. The coupler input member 6' presses the coupler intermediate member 7' out of the frictional-lock blocking engagement with the decoupling member 11', against the force of the restoring member 10'. Once the blocking engagement between the conical areas of the two members 7' and 11' has been released and the coupler engagement therefore completely established, the blocking member 34 abuts the casing part 4. In the final phase of the triggering movement which then follows, the triggering element 28 presses the blocking member 24 out of the blocking engagement with the blocking member 34 via the connecting part 33.

As soon as the rotational block formed by the blocking members 24 and 34 is released, the rotational drive movement of the coupler input member 6' is initiated due to the drive force of the drive member 25 and is transferred onto the coupler output member 9 via the coupler engagement. Because it is guided, —such that it is secured against rotating—in the linear guide 4a, the piston rod 15 is moved—in the threaded engagement with the coupler output member 9—in the advancing direction V, and product is delivered. This delivery movement is terminated by the stopping member 27 abutting the stopper 24c of the blocking member 24 which determines the zero dosage.

FIG. 21 shows the injection apparatus when a zero dosage or a small priming dosage is set, in the coupled state after the rotational block has been released, i.e. after the triggering element 28 has completely performed the triggering movement. If, advantageously, pressure is continuously exerted on the triggering element 28, the triggering sequence described above progresses automatically, from injecting to completely delivering the dosage set.

FIG. 23 shows the injection apparatus after the container 2 has been emptied. The casing part 1 has already been removed from the casing part 4. The piston rod 15 assumes its most distal position. The decoupling member 11' blocks the coupler input member 6' in the position retracted from the coupler intermediate member 7'. The functionality of the decoupling member 11' corresponds to that in the other embodiments. Unlike the two first embodiments, however, the casing part 1 and the decoupling member 11' are not directly in a guiding engagement with each other, but rather via an adaptor structure 36. The adaptor structure 36 is a sleeve in the casing part 4 which is fixed in and counter to the direction of the coupler movement X in the connecting portion, but can be rotated about the central longitudinal axis R of the casing part 4. The adaptor structure 35 forms a guiding curve 36a either as a cavity on or a breach in its shell area facing the decoupling member 11'. The guiding curve 35a exhibits the course of a threaded portion. The length measured over the circumference and the pitch of the guiding curve 35a measured with respect to the central longitudinal axis of the casing part 4 are dimensioned such that the decoupling member 11' is moved into the decoupling position shown in FIG. 21 by a quarter to a half revolution of the adaptor structure 35 relative to the decoupling member 11'. For generating the axial movement, the decoupling member 11' engages via its engaging element 12 with the guiding curve 35a. In this respect, reference is made to the statements regarding the first embodiment.

When connecting the casing parts 1 and 4, the adaptor structure 35 forms a linear guide for the casing part 1. The casing part 1 is inserted into the adaptor structure 35, wherein a slight frictional lock and correspondingly a sliding guide for the casing part 1 exists. The casing part 1 cannot be rotated about the central longitudinal axis of the casing part 4 relative to the adaptor structure 35. The engagement, which is rotationally secured accordingly, is established right at the beginning of inserting the casing part 1 into the adaptor structure 35. Once the casing part 1 has been inserted until it abuts against the casing part 4, i.e. once the coupler is accommodated at 4a, the casing part 1 is rotated relative to the casing part 4 and slaves the adaptor structure 36 during this rotational movement, until the engaging element 12 of the decoupling member 11' abuts the end of the guiding curve 36a. The rotational movement of the casing part 1 is, in some preferred embodiments, not possible until its axial abutting position, for which purpose a rotational block acting up until the abutting position can also be formed between the casing parts 1 and 4.

The movement of the decoupling member 11' caused in the guiding engagement exhibits an axial length which is greater than the length X of the complete coupler movement. In its decoupling movement, the decoupling member 11' presses the coupler input member 6' beyond its holding position as assumed in the resting state, and blocks it in said decoupling position. In this forced decoupling movement, the coupler input member 6' slaves the triggering element 28 via the stopper element 29b. Via the latch between the slaving means 29c and 34a, the blocking member 34 is also slaved, against the force of the blocking spring 31, and moved out of the blocking engagement. The blocking member 24 cannot follow the blocking member 34, since it is abutting against the casing part 4. Detaching the casing parts 1 and 4 thus releases the rotational block by the decoupling mechanism which the casing parts 1 and 4 form with the decoupling member 11' via the adaptor structure 35. If the coupler input member 6' has not yet assumed the zero dosage position, it is rotated now at the latest into the zero dosage position by the drive member 25, and the dosage display 20" is zeroed. In this respect, reference may again be made to the particular advantage of the coupling between the dosage display 20" and the coupler input member 6', namely that for each delivery, the dosage display 20" is reset in accordance with the delivered dosage. If, one time, the dosage set was not delivered, for example because the injection process was aborted or the container 2 no longer contained the complete dosage set, the user can read this from the dosage display 20" which is then only partially reset.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering a fluid product, said device comprising:

a) a housing comprising a first casing part and a second casing part connected to the first casing part;

b) a linear guide formed directly by the housing;

c) a piston rod arranged in the housing and configured to be driven in an advancing direction;

d) a drive member configured to cause the piston rod to be driven in a delivery movement, wherein the drive member is configured as a unitary sleeve and comprises a thread, wherein the linear guide is configured to cause the drive member to be linearly guided relative to the housing in and counter to the advancing direction; and e) a coupler comprising a coupler input member adapted to couple the drive member to the piston rod in a coupler engagement, wherein the coupler input member is adapted to transfer a drive force of the drive member onto the piston rod, wherein the coupler input member is sleeve-shaped and comprises a thread complementary to the thread of the drive member, and wherein the coupler input member is in a threaded engagement with the drive member such that a linear drive movement of the drive member causes a rotational movement of the coupler input member;

f) wherein the coupler input member is coupled to the piston rod such that the rotational movement of the coupler input member causes the delivery movement of the piston rod; and g) a dosing member for setting a product dosage deliverable by operating or triggering the drive member, wherein during dose setting the dosing member is rotationally secured to the coupler input member such that the coupler input member rotates with the dosing member.

2. The device according to claim 1, wherein during a dosing movement, the drive member is guided linearly by the linear guide in a movement counter to the advancing direction.

3. The device according to claim 1, wherein during a dosing movement, the coupler input member rotates.

4. The device according to claim 1, wherein during a dosing movement, the coupler input member rotates and the drive member is caused to be moved counter to the advancing direction and guided linearly by the linear guide.

5. The device according to claim 1, wherein during the delivery movement, the piston rod is guided linearly in the advancing direction.

6. The device according to claim 1, wherein the threaded engagement between the coupler input member and the drive member is a first threaded engagement, and further comprising a second threaded engagement between the piston rod and the coupler, and wherein the linear drive movement of the drive member causes a rotational movement of the coupler in the second threaded engagement thereby causing the delivery movement of the piston rod.

7. The device according to claim 6, wherein during the delivery movement, the piston rod is guided linearly in the advancing direction.

8. The device according to claim 1, wherein the threaded engagement is not self-locking, such that in the threaded engagement, the drive member can be axially moved by a drive force acting on the drive member in the direction of a threaded axis.

9. The device according to claim 1, further comprising a dosage display for displaying a settable product dosage.

10. The device according to claim 1, further comprising a dosage display for displaying a settable product dosage.

11. The device according to claim 10, wherein the dosage display is an optical display.

12. A device for administering a fluid product, said device including:

a. a housing comprising a first casing part and a second casing part connected to the first casing part;

b. a linear guide formed directly by the housing;

c. a piston rod arranged in the housing and configured to be driven in an advancing direction;

d. a drive member configured to cause the piston rod to be driven in a delivery movement, wherein the drive member is configured as a unitary sleeve and comprises a thread, wherein the linear guide is configured to cause the drive member to be linearly guided relative to the housing in and counter to the advancing direction;

e. a coupler input member adapted to couple the drive member to the piston rod in a coupler engagement, wherein the coupler input member is adapted to transfer a drive force of the drive member onto the piston rod, wherein the coupler input member is sleeve-shaped and comprises a thread complementary to the thread of the drive member, and wherein the coupler input member is in a threaded engagement with the drive member such that a linear drive movement of the drive member causes a rotational movement of the coupler input member;

f. wherein the piston rod is linearly guided during the delivery movement, such that the piston rod is secured against rotating; and g. a dosing member for setting a product dosage deliverable by operating or triggering the drive member, wherein during dose setting the dosing member is rotationally secured to the coupler input member such that the coupler input member rotates with the dosing member.

13. The device according to claim 12, wherein during a dosing movement, the drive member is guided linearly by the linear guide in a movement counter to the advancing direction.

14. The device according to claim 12, wherein during a dosing movement, the coupler input member rotates.

15. The device according to claim 12, wherein during the delivery movement, the piston rod is guided linearly in the advancing direction.

16. The device according to claim 12, wherein the threaded engagement between the coupler input member and the drive member is a first threaded engagement, and further comprising a second threaded engagement between the piston rod and a coupler comprising the coupler input member, and wherein the linear drive movement of the drive member causes a rotational movement of the coupler in the second threaded engagement thereby causing the delivery movement of the piston rod.

17. The device according to claim 12, wherein the threaded engagement is not self-locking, such that in the threaded engagement, the drive member can be axially moved by a drive force acting on the drive member in a direction of a threaded axis.

18. The device according to claim 12, further comprising a dosage display for displaying a settable product dosage.

* * * * *